(12) United States Patent
Jordan et al.

(10) Patent No.: US 9,180,118 B2
(45) Date of Patent: Nov. 10, 2015

(54) THIADIAZOLIDINONE DERIVATIVES

(75) Inventors: Craig Jordan, Rochester, NY (US); Monica Guzman, Rochester, NY (US)

(73) Assignee: University of Rochester, Rochester, NY (US)

( * ) Notice: Subject to any disclaimer, the term of this patent is extended or adjusted under 35 U.S.C. 154(b) by 1188 days.

(21) Appl. No.: 12/374,002

(22) PCT Filed: Jul. 18, 2007

(86) PCT No.: PCT/US2007/016391
§ 371 (c)(1),
(2), (4) Date: Nov. 9, 2009

(87) PCT Pub. No.: WO2008/011113
PCT Pub. Date: Jan. 24, 2008

(65) Prior Publication Data
US 2010/0063109 A1 Mar. 11, 2010

Related U.S. Application Data

(60) Provisional application No. 60/831,893, filed on Jul. 18, 2006.

(51) Int. Cl.
*A61K 31/433* (2006.01)
*A61K 31/41* (2006.01)
*A61K 31/4164* (2006.01)

(52) U.S. Cl.
CPC .............. *A61K 31/41* (2013.01); *A61K 31/4164* (2013.01); *A61K 31/433* (2013.01)

(58) Field of Classification Search
CPC .................................................. A61K 31/433
See application file for complete search history.

(56) References Cited

U.S. PATENT DOCUMENTS

| 2003/0195238 A1 | 10/2003 | Gil et al. | |
|---|---|---|---|
| 2005/0014803 A1* | 1/2005 | Martinez et al. | 514/363 |
| 2005/0222220 A1* | 10/2005 | Padilla et al. | 514/362 |
| 2006/0204980 A1* | 9/2006 | Altieri et al. | 435/6 |
| 2007/0196514 A1* | 8/2007 | Li | 424/722 |

FOREIGN PATENT DOCUMENTS

| AU | 1507799 | 7/1999 |
|---|---|---|
| WO | 99/30739 | 6/1999 |
| WO | 01/70727 | 9/2001 |
| WO | 01/85685 | 11/2001 |
| WO | 2006/045581 A1 * | 5/2006 |

OTHER PUBLICATIONS

Dugo et al. Crit. Care Med., 2005, vol. 33, pp. 1903-1912.*
Guzman, et al., "Rapid Loss of Membrane Integrity and Irreversible Commitment to Cell Death of Primary AML Stem Cells: A Novel Activity for 4-benzyl, 2-methyl,1,2,4-Thiadiazolidine,3,5 Dione (TDZD-8)," *Blood*, 2006, 108:Abstract 2535.
Martinez et al., "SAR and 3D-QSAR Studies on Thiadiazolidinone Derivatives: Exploration of Structural Requirements for Glycogen Synthase Kinase 3 Inhibitors," *J. Med. Chem.*, 2005, 48:7103-7112.
Armitage et al., "Treatment of Refractory Adult Acute Nonlymphoblastic Leukemia with Subcutaneous 5-Azacytidine," *Cancer Treatment Report*, 1977, 61:1721-1723.
Buckley et al., "Improvement in Outcome for Children with Acute Nonlymphocytic Leukemia: A Report from the Childrens Cancer Study Group," *Cancer*, 1989, 1457-1465.
Gambari et al., "Human Leukemia K-562 Cells: Induction of Erythroid Differentiation by 5-Azacytidine," *Cell Differentiation*, 1984, 14:87-97.
Gaynon et al., "Continuous Infusion of 5-Azacytidine as Induction for Acute Nonlymphocytic Leukemia in Patients with Previous Exposure to 5-Azacytidine," *Oncology*, 1983, 40:192-194.
Ghosh et al., "Activation of p53-dependent apoptosis by acute ablation of glycogen synthase kinase-3beta in colorectal cancer cells," *Clin. Cancer Res.*, 2005, 11:4580-4588.
Hirschfeld et al., "Regulatory Approvals of Pediatric Oncology Drugs: Previous Experience and New Initiatives," *Journal of Clinical Oncology*, 2003, 21:1066-1073.
Kritz et al., "Pilot Study of 5-Azacytidine (5-AZA) and Carboplatin (CBDCA) in Patients with Relapsed/Refractory Leukemia," *American Journal of Hematology*, 1996, 51:117-121.
Martinez et al., "First Non-ATP Competitive Glycogen Synthase Kinase 3β(GSK-3β) Inhibitors: Thiadiazolidinones (TDZD) as Potential Drugs for the Treatment of Alzheimer's Disease," 2002, *Journal of Medicinal Chemistry*, 45:1292-1299.
Pinto et al., "5-Aza-2'-Deoxycytidine (Decitabine) and 5-Azacytidine in the Treatment of Acute Myeloid Leukemias and Myelodysplatic Syndromes: Past, Present and Future Trends," *Leukemia*, 1993, 7:51-60.
Raj et al., "Azacytidine (Vidaza®) in the Treatment of Myelodysplastic Syndromes," *Therapeutics and Clinical Risk Management*, 2006, 2:377-388.
Saiki et al., "Effect of Schedule on Activity and Toxicity of 5-Azacytidine in Acute Leukemia: A Southwest Oncology Group Study," *Cancer*, 1981, 47:1739-1742.
Silverman et al., "Randomized Controlled Trial of Azacitidine in Patients with the Myelodysplastic Syndrome: A Study of the Cancer and Leukemia Group B," *Journal of Clinical Oncology*, 2002, 20:2429-2440.

* cited by examiner

*Primary Examiner* — James D Anderson
(74) *Attorney, Agent, or Firm* — Riverside Law LLP

(57) ABSTRACT

The present invention relates to compounds of the formulae herein, their acceptable salts, solvates, hydrates and polymorphs thereof. The compounds of this invention are useful in treatment of disease, particularly leukemia. The invention also provides compositions comprising a compound of this invention and the use of such compositions in methods of treating disease, disorders, or symptoms thereof in a subject.

5 Claims, 15 Drawing Sheets

TDZD-8 inhibits growth of leukemic but not normal progenitor cells

Primary human cells treated with TDZD-8 and assayed for colony-forming units (CFU). Values shown are normalized to untreated controls (UT). nMyeloid = normal myeloid, nErythroid = normal erythroid.

TDZD-8 inhibits the engraftment and growth of leukemia stem cells but not normal hematopoietic stem cells in NOD/SCID mice Primary AML (#1-3) and normal (CB #1-3) specimens transplanted into NOD/SCID mice. Shown are levels of human cell engraftment in marrow of mice at 5-6 weeks post-transplant.

Exposure to TDZD-8 for as little as 30 minutes is sufficient to induce irreversible death of primary human CD34+CD38- AML cells In vitro cultures of human AML cells exposed to TDZD-8 for the indicated times, viability for primitive cells (CD34+CD38-) was determined at 24hours of culture. Values shown are normalized to untreated controls.

Exposure to TDZD-8 for as little as 30 minutes is sufficient to induce irreversible death in AML progenitor cells Colony-forming unit (CFU) assays of primary human AML cells treated for the indicated times with TDZD-8. Values shown are normalized to untreated controls.

TDZD-8 causes rapid loss of membrane integrity

Primary human AML cells treated for the indicated times with TDZD-8. Shown is uptake of vital dyes propidium iodide (PI), Hoechst 33342, and YoPro-1. Also shown is labeling with Annexin V.

TDZD-8 induces oxidative stress in human leukemia cells by rapid depletion of free thiol groups In vitro cultures of primary human AML cells treated for the indicated times with TDZD-8. Values shown indicate the reduction in labeling with mBBr.

Figure 11.
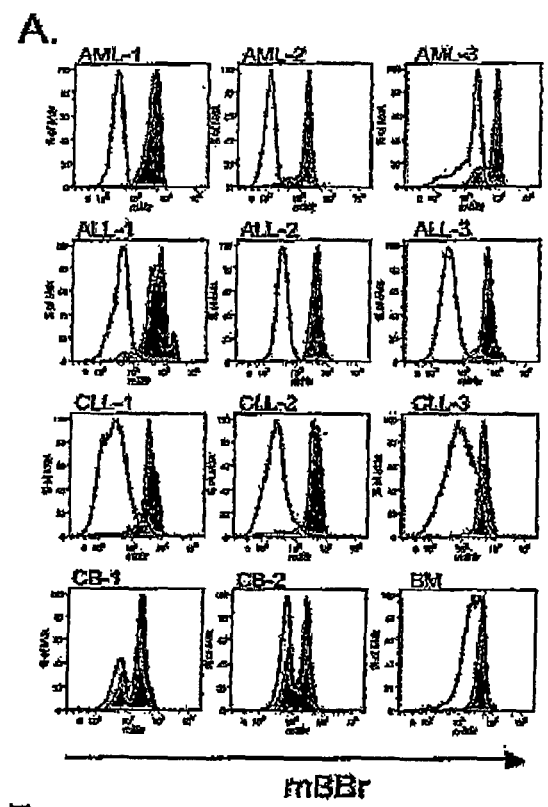
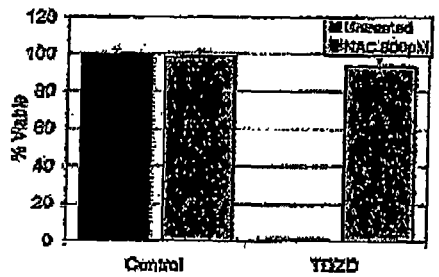

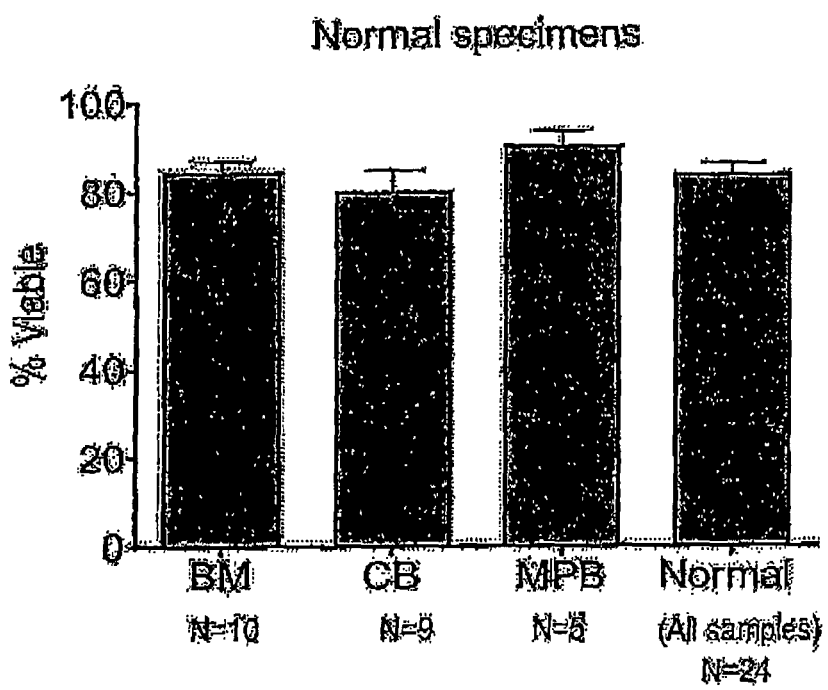

Figure 14. TDZD-8 does not induce cell death of primary mononuclear cells from specimens. Normal (healthy donors) specimens obtained from BM, CB or MPB specimens as indicated were cultured for 18-24 hours in the presence of 20µM TDZD-8. Cell viability was assessed by Annexin V/7-AAD staining. Percent viability is represented relative to untreated control. Error bars represent the SEM.

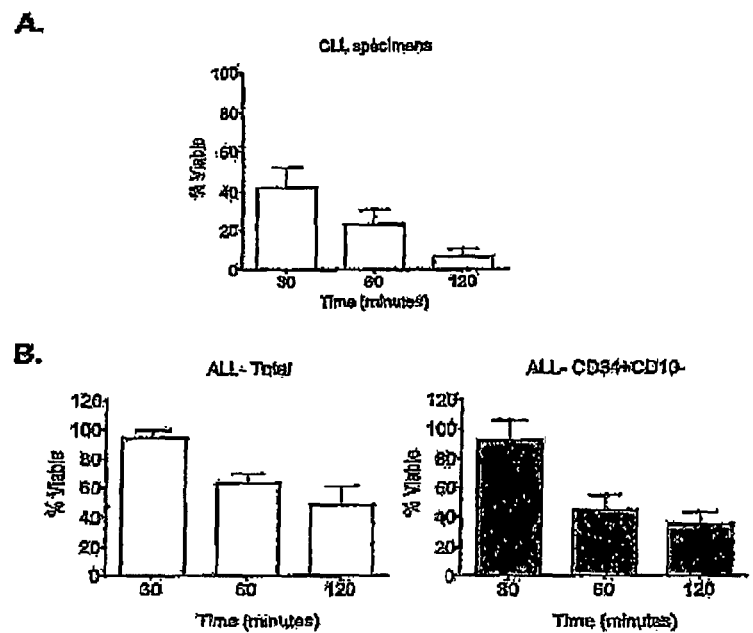

Figure 15. TDZD-8 induces cell death in primary lymphoid malignancies with rapid kinetics. (A) CLL (n=4) and (B) ALL (n=3) specimens were treated with 20μM TDZD=8 at the indicated time points. Viability was assessed using Annexin V/7-AAD stain. To assay phenotypically described stem cells, samples were co-stained and gated for indicated surface antibodies. Error bars represent the SEM.

THIADIAZOLIDINONE DERIVATIVES

STATEMENT REGARDING FEDERALLY SPONSORED RESEARCH OR DEVELOPMENT

Research supporting this application was carried out in part by funding provided by the United States of America as represented by the Secretary, Department of Health and Human Services under grant NIH R01CA90446. The government may have certain rights in the invention.

TECHNICAL FIELD OF THE INVENTION

The present invention relates to compounds of the formulae herein, their acceptable salts, solvates, hydrates and polymorphs thereof. The compounds of this invention are useful in treatment of disease, particularly leukemia. The invention also provides compositions comprising a compound of this invention and the use of such compositions in methods of treating disease, disorders, or symptoms thereof in a subject.

BACKGROUND OF THE INVENTION

Certain 2,4-disubstituted thiadiazolidinone (TDZD) compounds have been reported to be useful as enzyme inhibitors of glycogen synthase kinase 3β, or GSK-3. See, e.g., US 2003/0195238A1, US 2005/0222220A1. Glycogen synthase kinase-3 (GSK-3) is a serine/threonine protein kinase comprised of α- and β-isoforms that are each encoded by distinct genes (Coghlan et al., Chemistry & Biology, 7, 793-803 (2000); Kim and Kimmel, Curr. Opinion Genetics Dev., 10, 508-514 (2000)). The threonine/serine kinase glycogen synthase kinase-3 (GSK-3) fulfills a pivotal role in various receptor-linked signalling pathways (Doble, B W, Woodgett, J R J. Cell Sci. 2003, 116:1175-1186). Dysregulation within these pathways is considered a crucial event in the development of several prevalent human disorders, such as type II diabetes (Kaidanovich O, Eldar-Finkelman H, Expert Opin. Ther. Targets, 2002, 6:555-561), Alzheimer's disease (Grimes C A, Jope R S, Prog. Neurobiol. 2001, 65:391-426), CNS disorders such as manic depressive disorder and neurodegenerative diseases, and chronic inflammatory disorders (Hoeflich K P, Luo J, Rubie E A, Tsao M S, Jin O, Woodgett J, Nature 2000, 406:86-90).

Additionally certain TDZD compounds are reported to be non-competitive GSK-3β inhibitors, which demonstrate promise as AD pharmacotherapy agents. Martinez, A. et al. *J. Med. Chem.*, 45, 1292-1299 (2002).

It is now discovered that TDZD compounds are useful in treating disorders different and distinguishable from those previously reported.

SUMMARY OF THE INVENTION

The present invention relates to new treatment methods relating to a compound of Formula I:

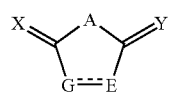

Formula I or a salt thereof; or a prodrug, or a salt of a prodrug thereof; or a hydrate, solvate, or polymorph thereof; wherein:

A is —C(R$^1$)$_2$—, —O— or —NR$^1$—; E is —NR$^1$— or —CR$^1$R$^2$— and the substituent R$^2$ is absent if - - - is a second bond between E and G; G is —S—, —NR$^1$— or —CR$^1$R$^2$— and the substituent R$^2$ is absent if - - - is a second bond between E and G; - - - may be a second bond between E and G where the nature of E and G permits and E with G optionally then forms a fused aryl group; R$^1$ and R$^2$ are each independently selected from hydrogen, alkyl, cycloalkyl, haloalkyl, aryl, —(Z)$_n$-aryl, heteroaryl, —OR$^3$, —C(O)R$^3$, —C(O)OR$^3$, —(Z)$_n$—C(O)OR$^3$ and —S(O)$_t$— or as indicated R$^2$ can be such that E with G then form a fused aryl group; Z is independently selected from —C(R$^3$)(R$^4$)—, —C(O)—, —O—, —C(=NR$^3$)—, —S(O)$_t$— and N(R$^3$)—; n is zero, one or two; t is zero, one or two; R$^3$ and R$^4$ are each independently selected from hydrogen, alkyl, aryl and heterocyclic; and X and Y are each independently selected from =O, =S, =N(R$^3$) and =C(R$^1$)(R$^2$).

The treatment methods include administration of a compound of any of the formulae herein, or a composition including a compound of any of the formulae herein, to a subject.

The invention also relates to compounds of any of the formulae herein, and compositions thereof, for use in treatment of a subject having a disease or disorder, and a compound of any formulae herein, for manufacture of a composition including a compound of any of the formulae herein useful for treatment of a subject.

BRIEF DESCRIPTION OF THE DRAWINGS

FIG. 11 TDZD-8 treatment induces oxidative stress. (A) Flow cytometric overlays for mBBr fluorescence on primary AML, CLL, ALL or normal mononuclear cells treated cells (20 μM TDZD; black bold lines) over untreated controls (black line/gray filling). (B) Percent viability of primary AML cells pre-treated with NAC (grey bars) for 1 h prior to treatment with 20 μM TDZD-8. Viability was determined 24 hours after the addition of each drug. Error bars represent the SEM.

FIG. 14 illustrates % viability of normal specimens, indicating that TDZD-8 does not induce cell death of primary mononuclear cells from normal specimens.

FIG. 15 illustrates % viability of: (A) CLL specimens; (B) ALL (total and CD34+CD10−) specimens indicating that TDZD-8 induces cell death in primary lymphoid malignancies with rapid kinetics.

DETAILED DESCRIPTION OF THE INVENTION

Figure 1:
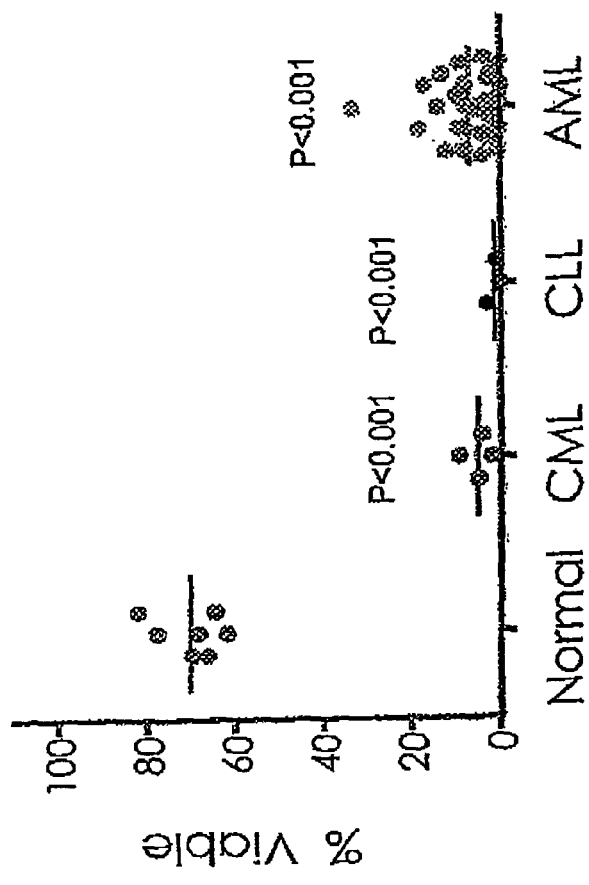
FIG. 1 illustrates results of human cell cultures treated with 4-benzyl-2-methyl-1,2,4-thiadiazolidine-3,5-dione (TDZD-8). TDZD-8 induces death of primary human leukemic cells but not normal cells.
Figure 2:
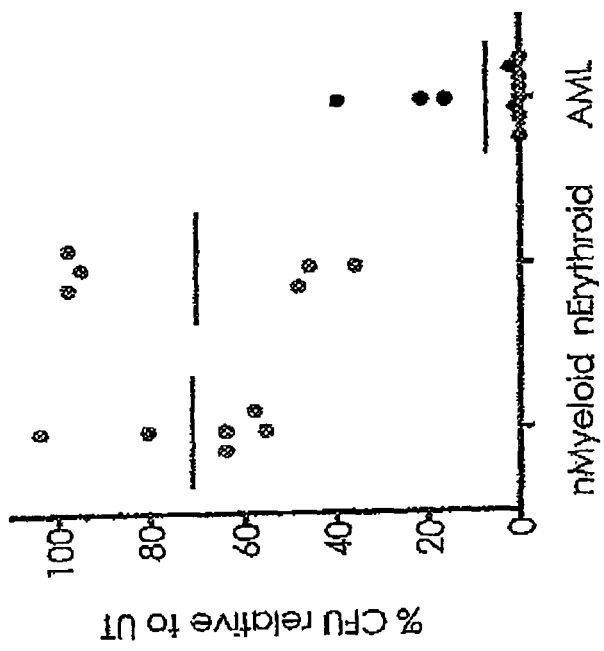
FIG. 2 illustrates results of human cells treated with TDZD-8. TDZD-8 inhibits growth of leukemic cells but not normal progenitor cells.
Figure 3:
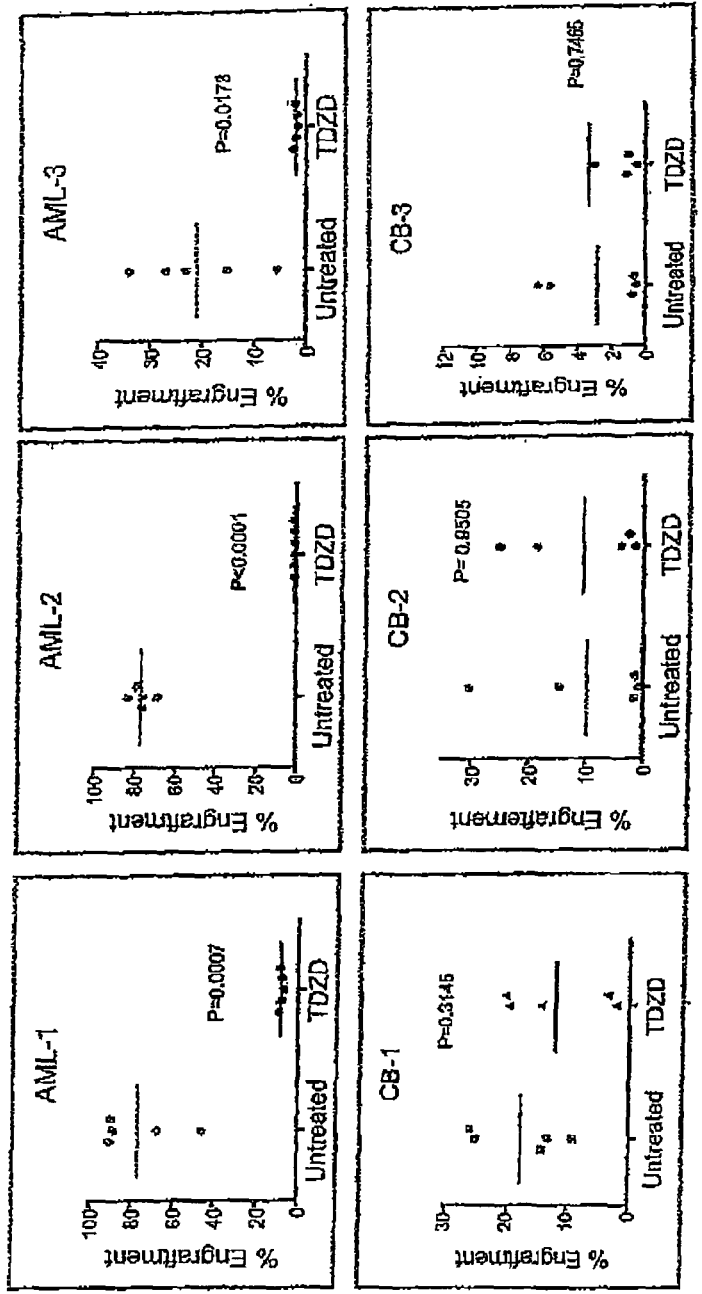
FIG. 3 illustrates results of human cell engraftment in NOD/SCID mice treated with TDZD-8. TDZD-8 inhibits the engraftment and growth of leukemia stem cells, but not normal hematopoietic stem cells.
Figure 4:
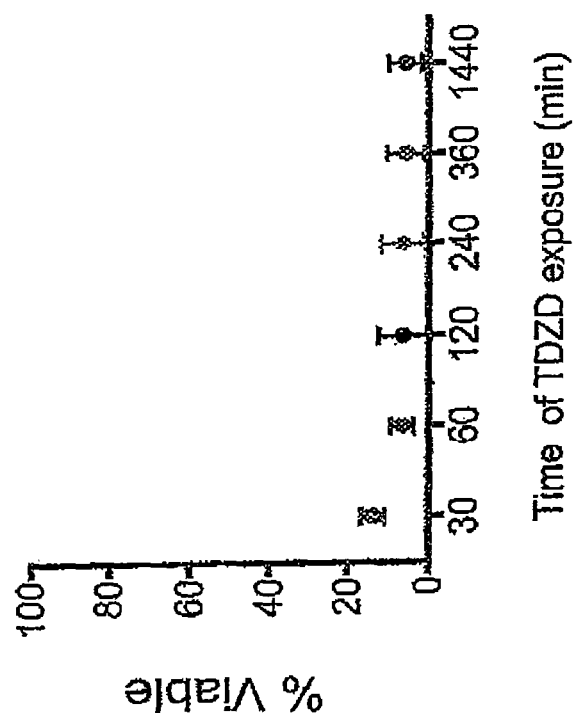
FIG. 4 illustrates results of treating human AML cells with TDZD-8. Exposure for as little as 30 minutes is sufficient to induce irreversible death of primary human CD34+CD38− AML cells.
Figure 5:
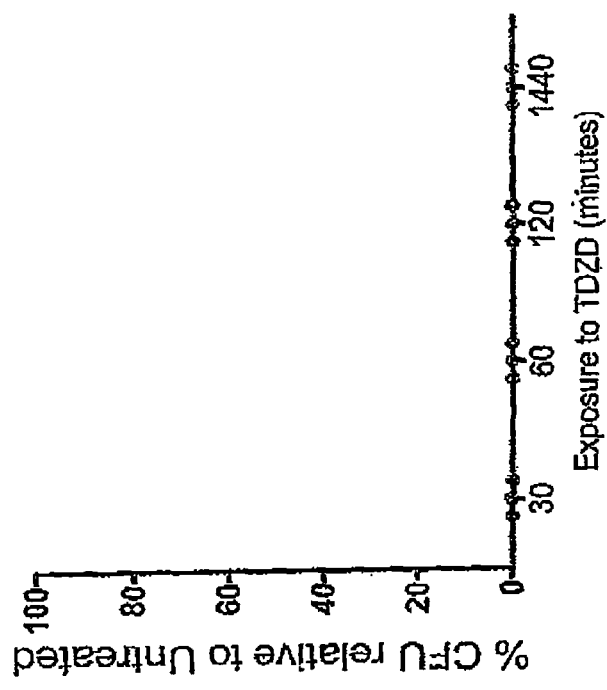
FIG. 5 illustrates results of treating human AML cells with TDZD-8. Exposure for as little as 30 minutes is sufficient to induce irreversible death in AML progenitor cells.
Figure 6:
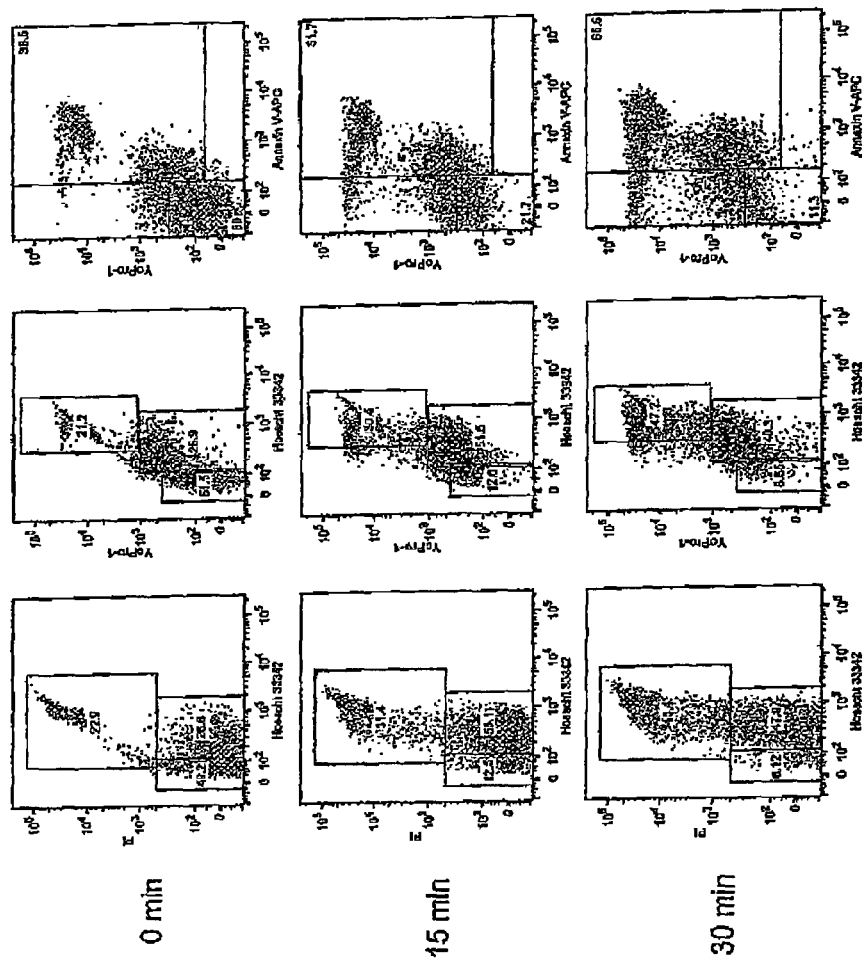
FIG. 6 illustrates results of treating human AML cells with TDZD-8. TDZD-8 causes rapid loss of membrane integrity.
Figure 7:
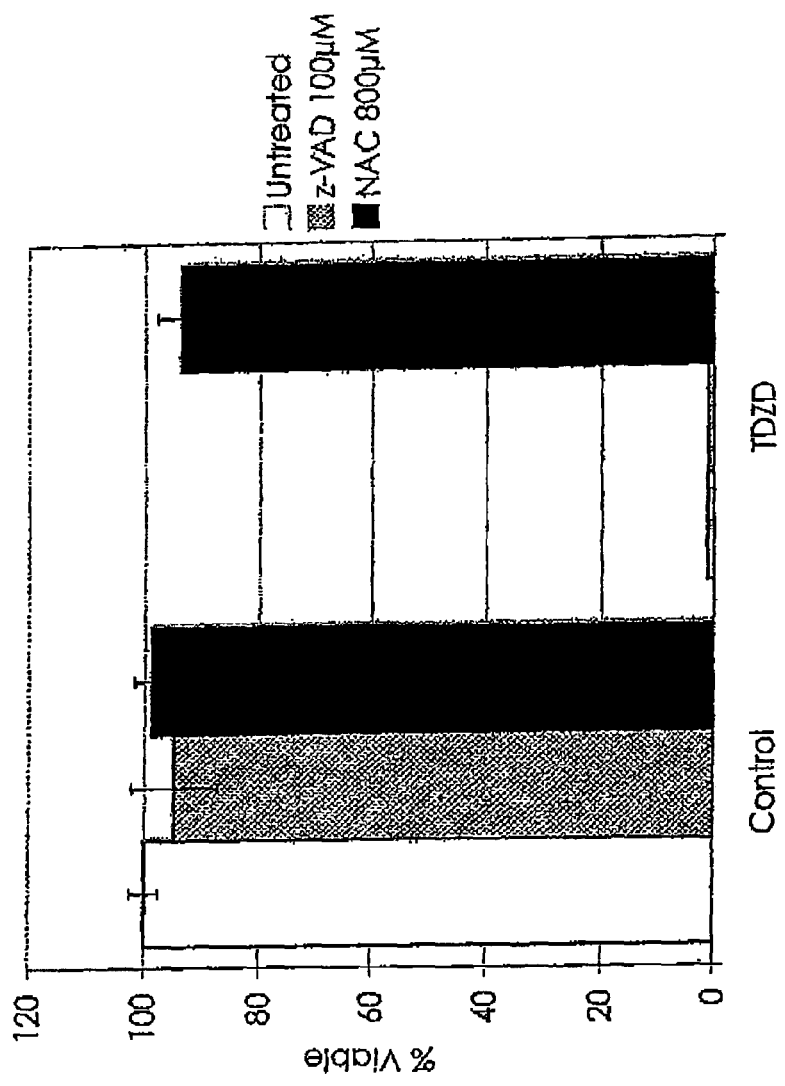
FIG. 7 illustrates results of treating human AML cells with TDZD-8. N-acetyl-cysteine but not Z-VAD can block TDZD-8 toxicity in primary AML cells.
Figure 8:
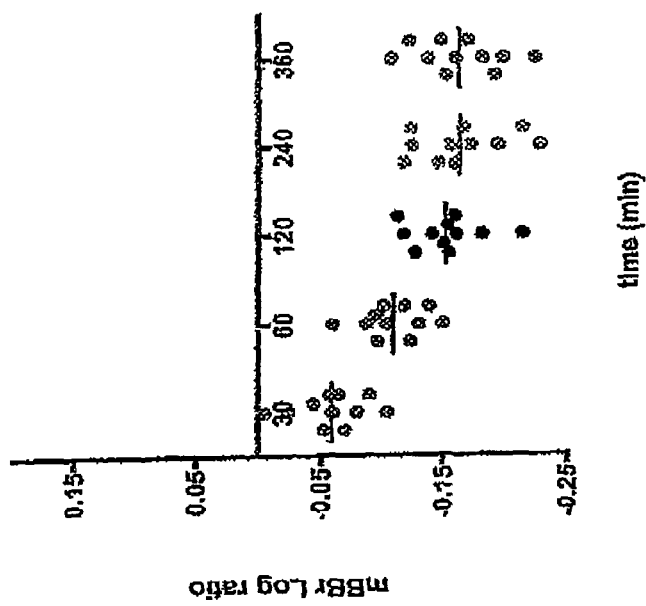
FIG. 8 illustrates results of treating human AML cells with TDZD-8. TDZD-8 induces oxidative stress in human leukemia cells by rapid depletion of free thiol groups.

The present invention provides an isolated compound of Formula I:

Formula (I)

or a salt thereof; or a prodrug, or a salt of a prodrug thereof; or a hydrate, solvate, or polymorph thereof; wherein:

A is —C(R$^1$)$_2$—, —O— or —NR$^1$—; E is —NR$^1$— or —CR$^1$R$^2$— and the substituent R$^2$ is absent if - - - is a second bond between E and G; G is —S—, —NR$^1$— or —CR$^1$R$^2$— and the substituent R$^2$ is absent if - - - is a second bond between E and G; - - - may be a second bond between E and G where the nature of E and G permits and E with G optionally then forms a fused aryl group; R$^1$ and R$^2$ are each independently selected from hydrogen, alkyl, cycloalkyl, haloalkyl, aryl, —(Z)$_n$-aryl, heteroaryl, —OR$^3$, —C(O)R$^3$, —C(O)OR$^3$, —(Z)$_n$—C(O)OR$^3$ and —S(O)$_t$— or as indicated R$^2$ can be such that E with G then form a fused aryl group; Z is independently selected from —C(R$^3$)(R$^4$)—, —C(O)—, —O—, —C(=NR$^3$)—, —S(O)$_t$— and N(R$^3$)—; n is zero, one or two; t is zero, one or two; R$^3$ and R$^4$ are each independently selected from hydrogen, alkyl, aryl and heterocyclic; and X and Y are each independently selected from =O, =S, =N(R$^3$) and =C(R$^1$)(R$^2$).

In one aspect of the formulae herein, X and Y are =O.

In another aspect of the formulae herein, A is —NR$^1$—.

In another aspect of the formulae herein, G is —S—.

In another aspect of the formulae herein, E is —NR$^1$—.

In another aspect of the formulae herein, A is —NR$^1$— and E is —NR$^1$—.

In another aspect of the formulae herein, G is —S—, A is —NR$^1$— and E is —NR$^1$—.

In another aspect of the formulae herein, each R$^1$ is independently alkyl.

In another aspect of the formulae herein, A is —NR$^1$— and E is —NR$^1$—, where one R$^1$ is independently alkyl and the other R$^1$ is independently alkyl substituted with aryl.

Another aspect is a compound of Formula (II):

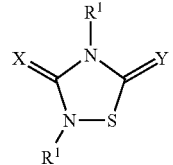

Formula (II)

or a salt thereof; or a prodrug, or a salt of a prodrug thereof; or a hydrate, solvate, or polymorph thereof; wherein:

each $R^1$ and $R^2$ are each independently selected from hydrogen, alkyl, cycloalkyl, haloalkyl, aryl, —$(Z)_n$-aryl, heteroaryl, —$OR^3$, —$C(O)R^3$, —$C(O)OR^3$, —$(Z)_n$—$C(O)OR^3$ and —$S(O)_t$— or as indicated $R^2$ can be such that E with G then form a fused aryl group; Z is independently selected from —$C(R^3)(R^4)$—, —$C(O)$—, —$C(=NR^3)$—, —$S(O)_t$— and $N(R^3)$—; n is zero, one or two; t is zero, one or two; $R^3$ and $R^4$ are each independently selected from hydrogen, alkyl, aryl and heterocyclic; and X and Y are each independently selected from =O, =S, =$N(R^3)$ and =$C(R^1)(R^2)$.

In another aspect of the formulae herein, each $R^1$ is independently selected from alkyl and substituted alkyl.

In another aspect of the formulae herein, each $R^1$ is independently selected from alkyl and aryl-substituted alkyl.

In another aspect of the formulae herein, each $R^1$ is independently selected from alkyl and phenyl-substituted alkyl.

In another aspect of the formulae herein one $R^1$ is independently alkyl and the other $R^1$ is independently arylalkyl.

Other aspects are the specifically listed compounds in Table I.

TABLE I

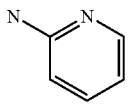

| Compound No. | $R^a$ | $R^b$ | X | Y |
|---|---|---|---|---|
| 1 | CH₂Ph | Me | O | O |
| 2 | Et | Me | O | O |
| 3 | Et | nPr | O | O |
| 4 | Et | cyclohexyl | O | O |
| 5 | Ph | Me | O | O |
| 6 | CH₂CO₂Et | Me | O | O |
| 7 | 4-OMePh | Me | O | O |
| 8 | CH₂Ph | Et | O | O |
| 9 | Et | iPr | O | O |
| 10 | CH₂Ph | Et | O | S |
| 11 | CH₂Ph | CH₂Ph | O | S |
| 12 | Ph | Ph | O | S |
| 13 | Et | Et | O | S |
| 14 | Cyclohexyl | Me | O | O |
| 15 | 4-MePh | Me | O | O |
| 16 | 4-BrPh | Me | O | O |
| 17 | 4-FPh | Me | O | O |
| 18 | 4-ClPh | Me | O | O |
| 19 | Et | Me | 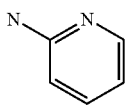 | O |
| 20 | Et | Et | 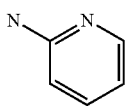 | O |
| 21 | Et | H | 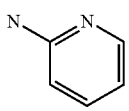 | O |
| 22 | Me | Me | 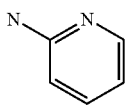 | O |
| 23 | Et | Me | 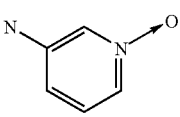 | O |
| 24 | Et | Me | 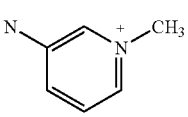 | O |

TABLE I-continued

[Structure: 1,2,4-thiadiazolidine ring with X=C at position 5, S at 1, N-R^b at 2, C=Y at 3, N-R^a at 4]

| Compound No. | $R^a$ | $R^b$ | X | Y |
|---|---|---|---|---|
| 25 | ET | Me | N-(1-methylpiperidin-3-yl) | O |
| 26 | Et | Me | N-(pyridin-2-yl) | S |
| 27 | Et | Et | O | O |
| 28 | Et | Et | O | S |
| 29 | Bn | Bn | O | O |
| 30 | $CH_2CO_2Et$ | Et | O | O |
| 31 | $CH_2Ph$ | COPh | O | O |
| 32 | Ph | Et | O | NH |
| 33 | $CH_2Ph$ | $CH_2CO_2Et$ | O | O |
| 34 | 4-$CF_3$Ph | Me | O | O |
| 35 | n-Bu | Et | O | O |
| 36 | $CH_2Ph$ | Et | O | N—OH |
| 37 | 3-BrPh | Me | O | O |
| 38 | 2-BrPh | Me | O | O |
| 39 | Ph | Et | O | NCONHEt |
| 40 | Ph | $CO_2Et$ | S | $NCO_2Et$ |
| 41 | $CH_2CH_2Ph$ | Et | O | O |
| 42 | $CH_2Ph$ | H | O | O |
| 43 | Ph | Et | O | O |
| 44 | $CH_2CO_2Et$ | $CH_2CO_2Et$ | O | O |
| 45 | $CH_2CO_2Et$ | Me | O | O |
| 46 | $CH_2CO_2Et$ | iPr | O | O |
| 47 | $CH_2CO_2Et$ | Bz | O | O |
| 48 | Naphthyl | Me | O | O |
| 49 | 4-$NO_2$Ph | Et | O | O |
| 50 | Ph | Et | O | N—OH |
| 51 | $CH_2Ph$ | iPr | O | O |
| 52 | Ph | Ph | O | O |
| 53 | 4-MeOPh | Et | O | O |
| 54 | 4-MePh | Et | O | O |
| 55 | 4-BrPh | Et | O | O |
| 56 | $CH_2Ph$ | $CH_2CH_2Ph$ | O | O |
| 57 | $CH_2Ph$ | $CH(Ph)_2$ | O | O |
| 58 | $CH_2Ph$ | naphthalen-1-yl | O | O |
| 59 | $CH_2Ph$ | 4-methoxybenzyl | O | O |
| 60 | $CH_2Ph$ | 2-t-butyl-6-methyl-phenyl | O | O |
| 61 | $CH_2Ph$ | 4-methylbenzyl | O | O |
| 62 | $CH_2Ph$ | 2-benzylphenyl | O | O |
| 63 | $CH_2PH$ | 2-benzo[1,3]dioxol-5-yl | O | O |
| 64 | $CH_2Ph$ | 4-phenoxyphenyl | O | O |
| 65 | Me | $CH_2Ph$ | O | O |

The term "compound" as used herein, is intended to mean stable chemical compounds.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines.

A prodrug salt is a compound formed between an acid and a basic group of the prodrug, such as an amino functional group, or a base and an acidic group of the prodrug, such as a carboxyl functional group. In a preferred embodiment, the prodrug salt is a pharmaceutically acceptable salt. According to another preferred embodiment, the counterion to the saltable prodrug of the compound of a formula herein is pharmaceutically acceptable. Pharmaceutically acceptable counterions include, for instance, those acids and bases noted herein as being suitable to form pharmaceutically acceptable salts.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucaronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates and solubility (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The compounds of the present invention can contain one or more asymmetric carbon atoms. As such, a compound of this invention can exist as the individual stereoisomers (enantiomers or diastereomers) as well a mixture of stereoisomers. Accordingly, a compound of the present invention will include not only a stereoisomeric mixture, but also individual respective stereoisomers substantially free from one another stereoisomers. The term "substantially free" as used herein means less than 25% of other stereoisomers, preferably less than 10% of other stereoisomers, more preferably less than 5% of other stereoisomers and most preferably less than 2% of other stereoisomers, are present. Methods of obtaining or synthesizing diastereomers are well known in the art and may be applied as practicable to final compounds or to starting material or intermediates. Other embodiments are those wherein the compound is an isolated compound.

The compounds herein may contain one or more asymmetric centers and thus occur as racemates and racemic mixtures, single enantiomers, individual diastereomers and diastereomeric mixtures. All such isomeric forms of these compounds are expressly included in the present invention. The compounds herein may also contain linkages (e.g., carbon-carbon bonds) wherein bond rotation is restricted about that particular linkage, e.g., restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention.

The compounds of the invention may be synthesized by well-known techniques or are commercially available. The starting materials and certain intermediates used in the synthesis of the compounds of this invention are available from commercial sources or may themselves be synthesized using reagents and techniques known in the art, including those synthesis schemes delineated herein. See, for instance, US 2003/0195238; US 2005/0222220, and references cited therein.

In one aspect, compounds are synthesized according to Scheme (I) or Scheme (II):

Scheme (I)

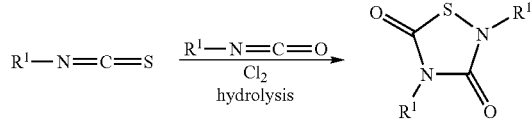

Scheme (II)

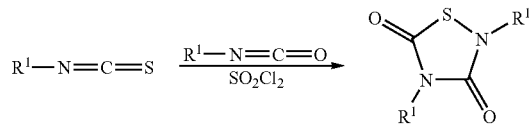

Definitions of variables in the structures in schemes herein are commensurate with those of corresponding positions in the formulae delineated herein.

The synthesized compounds can be separated from a reaction mixture and further purified by a method such as column chromatography, high pressure liquid chromatography, or recrystallization.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The specific approaches and compounds shown above are not intended to be limiting. Additional methods of synthesizing compounds of the formulae herein and their synthetic precursors, including those within routes not explicitly shown in Schemes herein, are within the means of chemists of ordinary skill in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL).

Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, $2^{nd}$ Edition, Carlson R, Ed, 2005; Elsevier Science Ltd.; Jähnisch, K et al, Angew. Chem. Int. Ed. Engl. 2004 43: 406; and references therein).

The synthetic methods described herein may also additionally include steps, either before or after any of the steps described in the synthetic schemes, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, chromatography).

Combinations of substituents and variables envisioned by this invention are only those that result in the formation of stable compounds. The term "stable", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition).

The term "alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents independently selected from the group consisting of a halo, hydroxy, alkoxy, carboxy, cyano, carbonyl, acyl, alkoxycarbonyl, amino, nitro, mercapto and alkylthio.

"Alkoxy" refers to a radical of the formula —ORa where Ra is an alkyl radical as defined above, e.g., methoxy, ethoxy, propoxy, etc.

"Alkoxycarbonyl" refers to a radical of the formula —C(O)ORa where Ra is an alkyl radical as defined above, e.g., methoxycarbonyl, ethoxycarbonyl, propoxycarbonyl, etc.

"Alkylthio" refers to a radical of the formula —SRa where Ra is an alkyl radical as defined above, e.g., methylthio, ethylthio, propylthio, etc.

"Amino" refers to a radical of the formula —NH$_2$.

"Aryl" refers to a phenyl or naphthyl radical, preferably a phenyl radical. The aryl radical may be optionally substituted by one or more substituents selected from the group consisting of hydroxy, mercapto, halo, alkyl, phenyl, alkoxy, haloalkyl, nitro, cyano, dialkylamino, aminoalkyl, acyl and alkoxycarbonyl, as defined herein.

"Aralkyl" refers to an aryl group linked to an alkyl group. Preferred examples include benzyl and phenethyl.

"Acyl" refers to a radical of the formula —C(O)—Rc and —C(O)—Rd where Rc is an alkyl radical as defined above and Rd is an aryl radical as defined above, e.g., acetyl, propionyl, benzoyl, and the like.

"Aroylalkyl" refers to an alkyl group substituted with —C(O)—Rd, where Rd is as defined above. Preferred examples include benzoylmethyl.

"Carboxy" refers to a radical of the formula —C(O)OH.

"Cyano" refers to a radical of the formula —CN.

"Cycloalkyl" refers to a stable 3- to 10-membered monocyclic or bicyclic radical which is saturated or partially saturated, and which consist solely of carbon and hydrogen atoms. Unless otherwise stated specifically in the specification, the term "cycloalkyl" is meant to include cycloalkyl radicals which are optionally substituted by one or more substituents independently selected from the group consisting of alkyl, halo, hydroxy, amino, cyano, nitro, alkoxy, carboxy and alkoxycarbonyl.

"Fused aryl" refers to an aryl group, especially a phenyl or heteroaryl group, fused to the five-membered ring.

"Halo" refers to bromo, chloro, iodo or fluoro.

"Haloalkyl" refers to an alkyl radical, as defined above, that is substituted by one or more halo radicals, as defined above, e.g., trifluoromethyl, trichloromethyl, 2,2,2-trifluoroethyl, 1-fluoromethyl-2-fluoroethyl, and the like.

"Heterocycle" refers to a heterocyclyl radical. The heterocycle refers to a stable 3- to 15-membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran. The heterocycle may be optionally substituted by $R^3$ and $R^4$ as defined above in the summary of the invention.

"Heteroaryl" refers to an aromatic heterocycle.

"Mercapto" refers to a radical of the formula —SH.

"Nitro" refers to a radical of the formula —NO$_2$.

"Stereoisomer" refers to both enantiomers and diastereomers

"Boc" refers to tert-butoxycarbonyl

"alkylene" refers to a straight, branched, or partially or wholly cyclic alkyl group which may contain one or more degrees of unsaturation in the form of cis, trans, or mixed cis, trans-double bonds, or triple bonds.

"Substituted" refers to any chemical structure or group (e.g, alkyl, aryl, heteroaryl, etc.) referenced herein where one or more atoms is replaced by one or more substituents independently selected from the group consisting of a halo, hydroxy, alkoxy, carboxy, cyano, carbonyl, acyl, alkoxycarbonyl, amino, nitro, mercapto and alkylthio.

The invention also provides compositions comprising an effective amount of a compound of any one of the formulae herein or a salt thereof; or a prodrug or a salt of a prodrug thereof; or a solvate, hydrate, or polymorph thereof, if applicable; an acceptable carrier. The carrier(s) must be "acceptable" in the sense of being compatible with the other ingredients of the formulation.

In a preferred embodiment, the invention provides a composition comprising a compound of any of the formulae herein, or a pharmaceutically acceptable salt, prodrug or pharmaceutically acceptable prodrug salt thereof; or a solvate, hydrate or polymorph of any of the foregoing and a pharmaceutically acceptable carrier, wherein said composition is formulated for pharmaceutical use ("a pharmaceutical composition"). A "pharmaceutically acceptable carrier" is a carrier that is compatible with the other ingredients of the composition and not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US Patents, some of which include, but are not limited to, U.S. Pat. Nos. 4,369,172; and 4,842,866; 5,807,574; and references cited therein. Coatings can be used for delivery of compounds to the intestine (see, e.g., U.S. Pat. Nos. 6,548,084, 6,638,534, 5,217,720, and 6,569,457, 6,461,631, 6,528,080, 6,800,663, and references cited therein), or they may be non-eroding and designed to allow release of an active agent by extrusion (see, e.g. U.S. Pat. No. 6,706,283).

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added. Surfactants such as sodium lauryl sulfate may be useful to enhance dissolution and absorption.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be administered in the form of suppositories for rectal or vaginal administration. These compositions can be prepared by mixing a compound of Formula I with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition will be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Application of the subject therapeutics may be local, so as to be administered at the site of interest. Various techniques can be used for providing the subject pharmaceutical compositions at the site of interest, such as injection, use of catheters, trocars, projectiles, pluronic gel, stents, sustained drug release polymers or other device which provides for internal access.

Thus, according to another embodiment, a compound of the formulae herein may be incorporated into a pharmaceutical composition for coating an implantable medical device, such as prostheses, artificial valves, vascular grafts, stents, or catheters. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings are optionally further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating or filling an implantable drug release device comprising the step of contacting said drug release device with a compound of a compound of any of the formulae herein or a pharmaceutical composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound of any of the formulae herein or a pharmaceutical composition of this invention, such that said compound is therapeutically active.

According to another embodiment, the invention provides an implantable drug release device impregnated with or containing a compound of any of the formulae herein or a pharmaceutical composition of this invention, such that said compound is released form said device and is therapeutically active.

Where an organ or tissue is accessible because of removal from the patient, such organ or tissue may be bathed in a medium containing a pharmaceutical composition of this invention, a pharmaceutical composition of this invention may be painted onto the organ, or a pharmaceutical composition of this invention may be applied in any other convenient way.

The present invention further provides pharmaceutical compositions comprising an effective amount of one or more compound of any of the formulae herein, in combination with an effective amount of one or more second therapeutic agents useful for treating or preventing a disease or disorder herein.

Also within the scope of this invention are pharmaceutical compositions comprising an effective amount of a compound of any of the formulae herein, or a pharmaceutically acceptable salt thereof; or a prodrug or a pharmaceutically acceptable salt of a prodrug thereof; or a solvate, hydrate, or polymorph thereof; in combination with an effective amount of a second therapeutic agent useful for treating a disorder or symptom thereof, reducing side effects due to a treatment regimen, and a pharmaceutically acceptable carrier. Additional therapeutic agents useful in combination with the compounds of this invention include, but are not limited to: kinase inhibitors (e.g. Gleevec, CEP-701, PKC412, etc.), heat shock protein inhibitors (17-AAG), farnesyltransferase inhibitors (zarnestra), histone deacetylase inhibitors (SAHA, depsipeptide, MS-275, etc), CDK inhibitors (flavopiridol), proteasome inhibitors (bortezomib), demethylating agents (decitabine, vidaza), Bcl-2 inhibitors (ABT-737), anthracyclines (adriamycin, daunorubicin, doxorubicin, idarubicin), cytarabine, etoposide, dexamethasone, methotrexate, thioguanine, 6-mercaptopurine, ATRA, gemcitabine, cyclophosphamide, cisplatin, vincristine, prednisone, mitoxantrone, bleomycin, 5-fluorouracil, and rituxan; a pharmaceutically acceptable salt of any of the said additional therapeutic agents; or combinations of two or more of the foregoing.

In another embodiment, the invention provides separate dosage forms of a compound of any of the formula herein and a second therapeutic agent, wherein said compound and said second therapeutic agent are associated with one another. The term "associated with one another" as used herein means that the separate dosage forms are packaged together in the same container (e.g., in separate blister packs attached to one another, in separate compartments of a compartmentalized container, in separate vessels contained in the same box, etc.), or otherwise attached to one another such that it is readily apparent that the separate dosage forms are intended to be sold and administered together (within less than 24 hours of one another, consecutively or simultaneously).

In the pharmaceutical compositions of the invention, a compound of any of the formulae herein is present in an effective amount. As used herein, the term "effective amount" refers to an amount which, when administered in a proper dosing regimen, is sufficient to reduce or ameliorate the severity, duration or progression, or enhance function compromised by a disorder, prevent the advancement of a disorder, cause the regression of a disorder, or enhance or improve the prophylactic or therapeutic effect(s) of another therapy.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabelling/assay techniques, blotting/chemiluminescence methods, real-time PCR, and the like.

The interrelationship of dosages for animals and humans (based on milligrams per meter squared of body surface) is described in Freireich et al., (1966) Cancer Chemother Rep 50: 219. Body surface area may be approximately determined from height and weight of the patient. See; e.g., Scientific Tables, Geigy Pharmaceuticals, Ardley, N.Y., 1970, 537. An effective amount of a compound of any of the formulae herein can range from about 0.001 mg/kg to about 500 mg/kg, more preferably 0.01 mg/kg to about 100 mg/kg, including a range with a high and low number within the aforementioned ranges, inclusive. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of that second therapeutic agent is between about 20% and 100% of the dosage normally utilized in a monotherapy regime using just that additional agent. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents listed above will act synergistically with the compounds of this invention. When this occurs, it will allow the effective dosage of the second therapeutic agent and/or the compound any of the formulae herein to be reduced from that required in a monotherapy. This has the advantage of minimizing toxic side effects of either the second therapeutic agent or a compound any of the formulae herein, synergistic improvements in efficacy, improved ease of administration or use and/or reduced overall expense of compound preparation or formulation.

Methods of Treatment

In one embodiment, the present invention provides a method of treating or preventing a disorder or symptom thereof in a subject (e.g., human, animal) comprising the step of administering to said subject an effective amount of a compound of any of the formulae herein, preferably as part of a composition additionally comprising a pharmaceutically acceptable carrier. Preferably this method is employed to treat a subject suffering from or susceptible to one or more diseases or disorders involving leukemia cells, leukemia stem cells, or related hematologic disorders.

The method can also be employed to treat a subject suffering from or susceptible to cancer cell growth, lymphoma, multiple myeloma, leukemia cell growth, proliferative diseases, blood cancers, cancers of the central nervous system, breast, prostate, liver, lung, pancreas, kidney, colon, testes, ovary, thyroid, head and neck, cervix, bone, skin, and stomach, and hematologic malignancies, or disorders such as acute myelogenus leukemia (AML), blast crisis leukemia (CML, both lymphoid and meloid forms of the disorder), acute lymphocytic leukemia (ALL), and chronic lymphocytic leukemia (CLL). Other embodiments include any of the methods herein wherein the subject is identified as in need of the indicated treatment.

The methods herein are useful to eradicate leukemia cells (e.g., human leukemia cells) and in one aspect involve contacting the leukemia cells with an agent (e.g., compounds and compositions of any of the formulae herein) capable of causing two simultaneous events: (i) permeabilization of cell membranes, and (ii) induction of oxidative stress. The methods herein are also those that involve one or more of: (i) rapid loss of membrane integrity, (ii) depletion of free thiols, or (iii) inhibition of either or both the PKC and FLT3 signaling pathways.

Another aspect of the invention is a compound of any of the formulae herein for use in inhibiting (including causing cell death) of leukemia cell (e.g., leukemia blast cells) populations (e.g., tumors) in a subject. Preferably that use is in the treatment or prevention in a subject of a disease, disorder or symptom set forth herein.

Another aspect of the invention is a compound of any of the formulae herein for use in inhibiting (including causing cell death) of leukemia stem cell populations in a subject. Preferably that use is in the treatment or prevention in a subject of a disease, disorder or symptom set forth herein.

The preferred therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a cancer or proliferative disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

Another aspect of the invention is the use of any of the formulae herein in the manufacture of a medicament for treating disease, causing cell death in leukemia cells, selectively causing cell death in leukemia cells (e.g., while not adversely affecting normal cells, with reduced or little toxicity to normal cells, leukemia cells not usually destroyed by other therapies, leukemia cells not usually destroyed by standard leukemia therapies) in a subject. Preferably, the medicament is used for treatment or prevention in a subject of a disease, disorder or symptom set forth herein.

In another embodiment, the method of treatment further comprises the step of administering to said patient one or more additional therapeutic agents which, alone or in combination with a compound of any of the formulae herein, are effective to treat a disease, disorder or symptom thereof delineated herein; and for reducing the side effects of a compound of any of the formulae herein, enhancing or potentiating the activity of a compound of any of the formulae herein, or for increasing the duration of pharmacological action of a compound of any of the formulae herein.

Additional agents include, for example, histone deacetylase inhibitors (e.g., sodium butyrate, MS-275, SAHA, aphacidin, depsipeptide, FK 228, trichostatin A), kinase inhibitors (e.g. Gleevec, CEP-701, PKC412, etc.), heat shock protein inhibitors (17-AAG), farnesyltransferase inhibitors (zarnestra), CDK inhibitors (flavopiridol), proteasome inhibitors (bortezomib), demethylating agents (decitabine, vidaza), Bcl-2 inhibitors (ABT-737), etc.

In yet another embodiment, the method of treatment comprises the step of administering to said patient one or more therapeutic agents which, alone or in combination with a compound of any of the formulae herein, are effective to treat one or more of non-GSK mediated diseases, disorders, or symptoms thereof.

In each of the above embodiments, the second therapeutic agent or agents may be administered together with a compound a compound of any of the formulae herein as part of a single dosage form or as separate dosage forms. Alternatively, the second therapeutic agent or agents may be administered prior to, consecutively with, or following the administration of a compound a compound of any of the formulae herein. In such combination therapy treatment, both the compounds of this invention and the second therapeutic agent(s) are administered by conventional methods. The administration of the second therapeutic agent(s) may occur before, concurrently with, and/or after the administration of the compound of a compound of any of the formulae herein. When the administration of the second therapeutic agent occurs concurrently with a compound of a compound of any of the formulae herein, the two (or more) agents may be administered in a single dosage form (such as a composition of this invention comprising a compound a compound of any of the formulae herein, a second therapeutic agent or agents as described above, and a pharmaceutically acceptable carrier), or in separate dosage forms. The administration of a composition of this invention comprising both a compound of a compound of any of the formulae herein and a second therapeutic agent(s) to a subject does not preclude the separate administration of said second therapeutic agent(s), any other therapeutic agent or any compound of this invention to said subject at another time during a course of treatment.

Effective amounts of second therapeutic agent or agents useful in the methods of this invention are well known to those skilled in the art and guidance for dosing may be found in patents referenced herein, as well as in Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the optimal effective-amount range of the additional agent(s).

Second therapeutic agents useful in the method of treatment are the same as those described above as part of combination compositions. The compounds herein are found to possess inhibitory activity against members of the kinase family of enzymes, and thus are useful in modulating kinase-mediated metabolic pathways and disease/disorder processes. Another aspect is a method of treating a kinase-mediated disease or disorder in a subject comprising administration to the subject of a compound herein. In other aspects, the kinase is, for example, AKT1 (PKB alpha), CHEK1 (CHK1), DYRK3, FLT3, GSK3B, KDR (VEGFR2), MAP4K4 (HGK), MAPK14 (p38 alpha), MAPKAPK2, MET (cMet), PHKG2, PIM1, PRKCA (PKC alpha), PRKCB1 (PKC beta1), PRKCB2 (PKC beta2), PRKCD (PKC delta), PRKCE (PKC epsilon), PRKG (PKC gamma), PRKCH (PKC eta), PRKCI (PKC iota), PRKCN (PKD3), PRKCQ (PKC theta), PRKCZ (PKC zeta), PRKCD1 (PKC mu), ROCK1, RPS6KA3 (RSK2), STK6 (Aurora A), or SYK.

Primary AML, blast crisis CML (bcCML), ALL, and CLL specimens demonstrated rapid induction of cell death upon treatment with TDZD-8. In addition, for myeloid leukemias, cytotoxicity was observed for phenotypically described stein/progenitor cells, in vitro colony-forming progenitors, and LSCs as defined by xenotransplantation assays. In contrast, no significant toxicity was observed for normal hematopoietic stem and progenitor cells. Notably, cell death was frequently evident within 2 hours or less of TDZD-8 exposure. Thus, other aspects of the compounds and methods herein include those wherein leukemia cells undergo cell death upon contact or exposure to the compounds/compositions herein, while normal cells are not similarly impacted. Also, methods wherein the leukemia cell death upon exposure to compounds herein is rapid (e.g., <6 hours, <5 hours, <4 hours, <3 hours, <2 hours, <1 hour, <30 minutes, <15 minutes, <5 minutes), and methods wherein the compound administered is capable of causing rapid leukemia cell death upon contact or exposure are contemplated.

According to another aspect, the invention provides a compound of a compound of any of the formulae herein and one or more of the above-described second therapeutic agents, either in a single composition or as separate dosage forms for use in the treatment or prevention in a subject of a disease, disorder or symptom set forth above.

In yet another aspect, the invention provides the use of a compound a compound of any of the formulae herein and one or more of the above-described second therapeutic agents in the manufacture of a medicament, either as a single composition or as separate dosage forms, for treatment or prevention in a subject of a disease, disorder or symptom set forth above.

The compounds of this invention may be readily assayed for biological activity by known methods. For instance, in vitro methods of determining cell cycle status (flow cytometry using labeling with propidium iodide or similar dyes), cytotoxicity (labeling with Annexin V, trypan blue, TUNEL, or similar reagents), progenitor frequency (methylcellulose or soft agar colony-forming unit—CFU—assays), cobblestone-area forming assays (CAFC), long term culture-initiating cell (LTC-IC) assays, etc.

Animal models of some of the foregoing indications involving aberrant proliferation of hematopoietic cells treatable by the invention include for example: non-obese diabetic-severe combined immune deficient (NOD/SCID) mice injected with primary human AML, ALL, or CML cells; inbred Sprague-Dawley/Charles University Biology (SD/Cub) rats (spontaneous T-cell lymphoma/leukemia model); Emu-immediate-early response gene X-1 (IEX-1) mice (T-cell lymphoma model); rabbits injected with cynomogulus-Epstein Barr virus (T-cell lymphoma model); transgenic mice expressing p210 bcr/abl (founder mice, ALL model; progeny mice, CML model); transgenic mice expressing TCL-1 (CLL model); NOD/SCID mice injected with OCI-Ly10 or related cell lines (Non-hodgkins lymphoma models); NOD/SCID/gammac null (NOG) mice injected with U266 cells or primary human myeloma cells (multiple myeloma model); and, C57B1/KaLwRij mice injected with 5T33 cells (multiple myeloma model). Each of the compounds of this invention may be tested in these or similar animal models.

In order that the invention might be more fully understood, the following examples are set forth. They are not intended to limit the scope of the invention and further examples will be evident to those of ordinary skill in the art.

EXAMPLE 1

FIG. 1 Protocol

A. AML cells, bcCML cells, CLL, normal bone marrow (BM), and umbilical cord blood (CB) were obtained from volunteer donors with informed consent or from the National Disease Research Interchange (NDRI). The cells were isolated and processed as described [1]. Briefly, samples were subjected to Ficoll-Paque (Pharmacia Biotech, Piscataway, N.Y.) density gradient separation to isolate mononuclear cells. The percent CD34 in the samples analyzed ranged from 20% to 80%. Fresh or thawed cells were cultured in serum-free medium (SFM) [2] for 1 h before the addition of drugs. All drug treatments were performed in triplicate. TDZD-8 (Calbiochem) was reconstituted in DMSO and subsequently diluted in phosphate buffer saline (PBS). Total viable cell numbers were determined using a flow cytometric apoptosis assay as described [3]. Briefly, after 18 h of treatment, specimens were labeled with anti-CD34-PE (Becton Dickinson, San Jose, Calif.) for 20 minutes. Cells were then washed in cold PBS and resuspended in 200 µl of annexin-V buffer. Annexin-V-fluorescein isothiocyanate (FITC) and 7-aminoactinomycin (7-AAD; Molecular Probes, Eugene, Oreg.) were added and the samples were incubated at room temperature for 15 minutes followed by analysis using a Becton Dickinson LSRII flow cytometer. The total number of events collected was 100,000. The percent viable cells was defined as AnnexinV$^{neg}$/7-AAD$^{neg}$ cells on total (ungated) cells and on gates set for CD34$^+$ populations.

[1] Jordan, C. T., et al., *The interleukin-3 receptor alpha chain is a unique marker for human acute myelogenous leukemia stem cells*. Leukemia, 2000. 14(10): p. 1777-84.

[2] Lansdorp, P. M. and W. Dragowska, *Long-term erythropoiesis from constant numbers of CD34+ cells in serum-free cultures initiated with highly purified progenitor cells from human bone marrow*. J. Exp. Med., 1992. 175: p. 1501-1509.

[3] Guzman, M. L., et al., *Nuclear factor-kappaB is constitutively activated in primitive human acute myelogenous leukemia cells*. Blood, 2001. 98(8): p. 2301-7.

B. Primary human AML, blast crisis CML, ALL and CLL cells, mobilized peripheral blood (MPB) and normal bone marrow (BM) cells were obtained from volunteer donors with informed consent. Additional samples were obtained from the Quebec Leukemia Cell Bank, which collects specimens from ten university and regional hospitals. They obtained PB or BM cells with informed consent from patients with different morphologic types of AML and ALL. Umbilical cord blood (CB) was obtained from the National Disease Research Interchange (NDRI), or with informed consent from volunteer donors at Rochester General Hospital. Mononuclear cells were isolated from the samples using Ficoll-Paque (Pharmacia Biotech, Piscataway, N.Y.) density gradient separation. In some cases cells were cryopreserved in freezing medium of Iscove's modified Dulbecco medium (IMDM), 40% fetal bovine serum (FBS), and 10% dimethylsulfoxide (DMSO) or in CryoStor™ CS-10 (VWR). Cells were cultured in serum-free medium (SFM)$^{34}$ for 1 h before the addition of drugs. TDZD-8 and Parthenolide were obtained from EMD chemicals (San Diego, Calif.) from Biomol (Plymouth Meeting, Pa.) respectively.

C. Flow Cytometry: Apoptosis assays were performed as described.[19] Briefly, after 18-24 h of treatment, specimens were labeling using anti-CD38-allophycocyanin (APC), CD34-PECy7, CD123-phycoerythin (PE) or CD10-flurescein isothiocyanate (FITC) (Becton Dickinson, San Jose, Calif.) for 15 minutes. Cells were washed in cold PBS and resuspended in 200 µl of annexin-V buffer (0.01M HEPES/NaOH, 0.14M NaCl, 2.5 mM CaCl$_2$) Annexin-V-FITC or Annexin V-PE (Becton Dickinson) and 7-aminoactinomycin (7-AAD; Molecular Probes, Eugene, Oreg.). Samples were then incubated at room temperature for 15 minutes and analyzed on a BD LSRII flow cytometer. Analyses for phenotypically described stem cell subpopulations were performed by gating CD34+/CD38−/CD123+, CD34+/CD10−, and CD34+/CD38− for AML, ALL and normal specimens respectively. To assess human cell engraftment in the NOD/SCID xenotransplant model, BM cells were blocked with the anti-Fc receptor antibody 2.4G2 and 25% human serum and then labeled with anti-human CD45-PE antibody (Becton Dickinson, San Jose, Calif.). Free-thiol analysis was performed by labeling cells with monobromobimane (mBBr) (Probes-Invitrogen). Phospho-FLT3 (Tyr591) Alexa Fluor-488 conjugate (Cell Signaling, Danvers, Mass.) was used for detection of active FLT3. For multispectral imaging flow cytometry, cells were stained with YoPro-1 (Probes-Invitrogen), 7-AAD, Drag 5 and CD45-PE. Membrane integrity assays were also performed by standard flow cytometry by staining with YoPro-1, Hoescht-33342, Propidium Iodide (PI) (Probes-Invitrogen) and annexin V-APC. Cells were analyzed using the Amnis Imagestream imaging cytometer (Amnis Corporation; Seattle, Wash.).

EXAMPLE 2

FIG. 2 Protocol

AML, normal cells or other specimens were cultured in SFM as above for 18 h in the presence or absence of 20 micromolar TDZD-8. Cells were then plated at 50,000 cells/ml in Methocult™ GF H4534 (1% methylcellulose in IMDM, 30% FBS, 1% BSA, 10$^{-4}$M 2-mercaptoethanol, 2 mM L-glutamine, 50 ng/ml rh stem cell factor, 10 ng/ml rh GM-CSF, 10 ng/ml rh IL-3-Stem Cell Technologies, Vancouver, B.C.) supplemented with 3 units/ml of erythropoietin and 50 ng/ml G-CSF (R&D Systems, Minneapolis, Minn.). Colonies were scored after 10-14 days of culture.

EXAMPLE 3

FIG. 3 Protocol

NOD/SCID (NOD.CB17-prdkdc scid/J) mice (Jackson Laboratories, Bar Harbor, Me.) were sub-lethally irradiated with 270 rad using a RadSource™ X-ray irradiator the day before transplantation. Cells to be assayed (AML or normal umbilical cord blood—CB) were injected via tail vein (5-10 million cells) in a final volume of 0.2 ml of PBS with 0.5% FBS. After 6-8 weeks, animals were sacrificed and BM was isolated. To analyze human cell engraftment, BM cells were blocked with anti-Fc receptor antibody 2.4G2 and 25% human serum, labeled with anti-human CD45, CD33 or CD19 antibodies (BD, San Jose, Calif.), and analyzed using a Becton Dickinson LSRII flow cytometer.

EXAMPLE 4

FIG. 4 Protocol

The same procedure as described in Example 1 was used except after the timepoints indicated on the horizontal axis, cells were washed in PBS to remove excess TDZD-8, and replated in pre-warmed SFM for a total of 24 hours.

EXAMPLE 5

FIG. 5 Protocol

The same procedure as described in Example 2 was used except, after the timepoints indicated on the horizontal axis, cells were washed in PBS to remove excess TDZD-8, and plated at 50,000 cells/ml in Methocult™ GF H4534.

EXAMPLE 6

FIG. 6 Protocol

AML cells were cultured as described in Example 1 for the indicated times with 20 micromolar TDZD-8. Cells were then washed with PBS and stained to assess membrane permeability using annexin V-Allophycocyanin (APC) and the vital dyes: Yo-Pro-1 (0.1 uM), Hoescht 33342 (2.5 ug/ml), and Propidium Iodide (0.5 ug/ml) (Molecular Probes).

EXAMPLE 7

FIG. 7 Protocol

Cultures were established and analyzed as described for Example 1; however, cells were pre-incubated with either n-acetylcysteine (Sigma) or z-vad (Calbiochem) for one hour prior to addition of TDZD-8.

EXAMPLE 8

FIG. 8 Protocol

AML or normal cells were cultured in SFM as above for the indicated time (horizontal axis) in the presence or absence of 20 micromolar TDZD-8. Intracellular thiol levels were assessed by flow cytometry after labeling with 50 μM monobromobimane (molecular probes).

Analysis of primary AML, blast crisis CML (bcCML), ALL, and CLL specimens demonstrated rapid induction of cell death upon treatment with TDZD-8. In addition, for myeloid leukemias, cytotoxicity was observed for phenotypically primitive cells, in vitro colony-forming progenitors, and LSCs as defined by xenotransplantation assays. In contrast, no significant toxicity was observed for normal hematopoietic stem and progenitor cells. Notably, cell death was frequently evident within 2 hours or less of TDZD-8 exposure. Cellular and molecular studies indicate that the mechanism by which TDZD-8 induces cell death involves rapid loss of membrane integrity, depletion of free thiols, and inhibition of both the PKC and FLT3 signaling pathways. We conclude that TDZD-8 employs a unique and previously unknown mechanism to rapidly target leukemia cells, including malignant stem and progenitor populations.

Kinase Assays: Single point and titration assays are performed using protocols (or essentially using protocols) know in the art for kinase activity profiling against a battery of kinase targets, including, for example, those specifically delineated herein. Such assays include, for example, those available from commercial sources, contract research laboratories, and the like. Representative results for TDZD-8 against a battery of kinase targets is delineated at Table 3.

Immunoblots. Cells were prepared and analyzed as previously described.[35] Membrane fractions were prepared using mem-PER eukaryotic membrane protein extraction kit as per manufacturer's instructions (Pierce; Rockford, Ill.). Blots were probed with phospho-PKC (pan) (beta II; Ser660), phospho-PKCalpha/betaII (Thr638/641), total PKCα, PKCβ and FLT3 (Santa Cruz Biotechnology, Calif.), Caspase-3 (Cell Signaling technologies; Danvers, Mass.); caspase-8 and PARP (BD bioscience), cleaved PARP (abcam) or anti-actin (AC-15; Sigma) antibodies.

Statistical analysis. Statistical analyses and graphs were performed using GraphPad Prism software (GraphPad Software, San Diego, Calif.). For statistical analysis the data was log transformed and analyzed by one-way ANOVA followed by Tukey post-hoc test. For 2 group comparisons, significance was determined by paired t-tests.

References:
1. Bonnet D, Dick J E. Human acute myeloid leukemia is organized as a hierarchy that originates from a primitive hematopoietic cell. Nat Med. 1997; 3:730-737.
2. Lapidot T, Sirard C, Vormoor J, et al. A cell initiating human acute myeloid leukaemia after transplantation into SCID mice. Nature. 1994; 367:645-648.
3. Sutherland H J, Blair A, Zapf R W. Characterization of a hierarchy in human acute myeloid leukemia progenitor cells. Blood. 1996; 87:4754-4761.
4. Cox C V, Evely R S, Oakhill A, Pamphilon D H, Goulden N J, Blair A. Characterization of acute lymphoblastic leukemia progenitor cells. Blood. 2004; 104:2919-2925.
5. Jiang X, Zhao Y, Smith C, et al. Chronic myeloid leukemia stem cells possess multiple unique features of resistance to BCR-ABL targeted therapies. Leukemia. 2007; 21:926-935.
6. Sincock P M, Ashman L K. Expression of c-Kit and functional drug efflux are correlated in de novo acute myeloid leukaemia. Leukemia. 1997; 11:1850-1857.
7. Lowenberg B, Sonneveld P. Resistance to chemotherapy in acute leukemia. Curr Opin Oncol. 1998; 10:31-35.
8. Fialkow P J, Jacobson R J, Papayannopoulou T. Chronic myelocytic leukemia: clonal origin in a stem cell common to the granulocyte, erythrocyte, platelet and monocyte/macrophage. AmJMed. 1977; 63:125-130.
9. Raaijmakers M H, de Grouw E P, Heuver L H, et al. Breast cancer resistance protein in drug resistance of primitive CD34+38– cells in acute myeloid leukemia. Clin Cancer Res. 2005; 11:2436-2444.
10. Abbott B L, Colapietro A M, Barnes Y, Marini F, Andreeff M, Sorrentino B P. Low levels of ABCG2 expression in adult AML blast samples. Blood. 2002; 100:4594-4601.
11. Holyoake T, Jiang X, Eaves C, Eaves A. Isolation of a highly quiescent subpopulation of primitive leukemic cells in chronic myeloid leukemia. Blood. 1999; 94:2056-2064.
12. Graham S M, Jorgensen H G, Allan E, et al. Primitive, quiescent, Philadelphia-positive stem cells from patients with chronic myeloid leukemia are insensitive to STI571 in vitro. Blood. 2002; 99:319-325.
13. Guan Y, Gerhard B, Hogge D E. Detection, isolation, and stimulation of quiescent primitive leukemic progenitor cells from patients with acute myeloid leukemia (AML). Blood. 2003; 101:3142-3149.
14. Guzman M L, Rossi R M, Karnischky L, et al. The sesquiterpene lactone parthenolide induces apoptosis of human acute myelogenous leukemia stem and progenitor cells. Blood. 2005; 105:4163-4169.
15. Killmann S A. Acute leukaemia: development, remission/relapse pattern, relationship between normal and leukaemic haemopoiesis, and the 'sleeper-to-feeder' stem cell hypothesis. Baillieres Clin Haematol. 1991; 4:577-598.

16. van Rhenen A, Feller N, Kelder A, et al. High stem cell frequency in acute myeloid leukemia at diagnosis predicts high minimal residual disease and poor survival. Clin Cancer Res. 2005; 11:6520-6527.
17. Seipelt G, Hofmann W K, Martin H, et al. Comparison of toxicity and outcome in patients with acute myeloid leukemia treated with high-dose cytosine arabinoside consolidation after induction with a regimen containing idarubicin or daunorubicin. Ann Hematol. 1998; 76:145-151.
18. Leopold L H, Willemze R. The treatment of acute myeloid leukemia in first relapse: a comprehensive review of the literature. Leuk Lymphoma. 2002; 43:1715-1727.
19. Guzman M L, Neering S J, Upchurch D, et al. Nuclear factor-kappaB is constitutively activated in primitive human acute myelogenous leukemia cells. Blood. 2001; 98:2301-2307.
20. Ghosh S, Karin M. Missing pieces in the NF-kappaB puzzle. Cell. 2002; 109 Suppl: S81-96.
21. Nakanishi C, Toi M. Nuclear factor-kappaB inhibitors as sensitizers to anticancer drugs. Nat Rev Cancer. 2005; 5:297-309.
22. Guzman M L, Swiderski C F, Howard D S, et al. Preferential induction of apoptosis for primary human leukemic stem cells. Proc Natl Acad Sci USA. 2002; 99:16220-16225.
23. Martinez A, Alonso M, Castro A, et al. SAR and 3D-QSAR studies on thiadiazolidinone derivatives: exploration of structural requirements for glycogen synthase kinase 3 inhibitors. J Med. Chem. 2005; 48:7103-7112.
24. Martinez A, Alonso M, Castro A, Perez C, Moreno F J. First non-ATP competitive glycogen synthase kinase 3 beta (GSK-3beta) inhibitors: thiadiazolidinones (TDZD) as potential drugs for the treatment of Alzheimer's disease. J Med. Chem. 2002; 45:1292-1299.
25. Evenson A R, Fareed M U, Menconi M J, Mitchell J C, Hasselgren P O. GSK-3beta inhibitors reduce protein degradation in muscles from septic rats and in dexamethasone-treated myotubes. Int J Biochem Cell Biol. 2005; 37:2226-2238.
26. Chin P C, Majdzadeh N, D'Mello S R. Inhibition of GSK3beta is a common event in neuroprotection by different survival factors. Brain Res Mol Brain Res. 2005; 137:193-201.
27. Dugo L, Collin M, Allen D A, et al. GSK-3beta inhibitors attenuate the organ injury/dysfunction caused by endotoxemia in the rat. Crit. Care Med. 2005; 33:1903-1912.
28. Dugo L, Abdelrahman M, Murch O, Mazzon E, Cuzzocrea S, Thiemermann C. Glycogen synthase kinase-3beta inhibitors protect against the organ injury and dysfunction caused by hemorrhage and resuscitation. Shock. 2006; 25:485-491.
29. Cuzzocrea S, Mazzon E, Di Paola R, et al. Glycogen synthase kinase-3beta inhibition attenuates the degree of arthritis caused by type II collagen in the mouse. Clin Immunol. 2006; 120:57-67.
30. Cuzzocrea S, Genovese T, Mazzon E, et al. Glycogen synthase kinase-3 beta inhibition reduces secondary damage in experimental spinal cord trauma. J Pharmacol Exp Ther. 2006; 318:79-89.
31. Dugo L, Collin M, Allen D A, et al. Insulin reduces the multiple organ injury and dysfunction caused by coadministration of lipopolysaccharide and peptidoglycan independently of blood glucose: role of glycogen synthase kinase-3beta inhibition. Crit. Care Med. 2006; 34:1489-1496.
32. Whittle B J, Varga C, Posa A, Molnar A, Collin M, Thiemermann C. Reduction of experimental colitis in the rat by inhibitors of glycogen synthase kinase-3beta. Br J. Pharmacol. 2006; 147:575-582.
33. Cuzzocrea S, Di Paola R, Mazzon E, et al. Glycogen synthase kinase 3beta inhibition reduces the development of nonseptic shock induced by zymosan in mice. Shock. 2007; 27:97-107.
34. Lansdorp P M, Dragowska W. Long-term erythropoiesis from constant numbers of CD34+ cells in serum-free cultures initiated with highly purified progenitor cells from human bone marrow. J Exp Med. 1992; 175:1501-1509.
35. Jordan C T, Upchurch D, Szilvassy S J, et al. The interleukin-3 receptor alpha chain is a unique marker for human acute myelogenous leukemia stem cells. Leukemia. 2000; 14:1777-1784.
36. Shoemaker R H. The NCI60 human tumour cell line anticancer drug screen. Nat Rev Cancer. 2006; 6:813-823.
37. Jorgensen H G, Holyoake T L. A comparison of normal and leukemic stem cell biology in Chronic Myeloid Leukemia. Hematol Oncol. 2001; 19:89-106.
38. Dick J E. Acute myeloid leukemia stem cells. Ann NY Acad. Sci. 2005; 1044:1-5.
39. Zhang S, Ong C N, Shen H M. Critical roles of intracellular thiols and calcium in parthenolide-induced apoptosis in human colorectal cancer cells. Cancer Lett. 2004; 208: 143-153.
40. Koivunen J, Aaltonen V, Peltonen J. Protein kinase C (PKC) family in cancer progression. Cancer Lett. 2006; 235:1-10.
41. Griner E M, Kazanietz M G. Protein kinase C and other diacylglycerol effectors in cancer. Nat Rev Cancer. 2007; 7:281-294.
42. Nishikawa M, Shirakawa S. The expression and possible roles of protein kinase C in haematopoietic cells. Leuk Lymphoma. 1992; 8:201-211.
43. Levis M, Murphy K M, Pham R, et al. Internal tandem duplications of the FLT3 gene are present in leukemia stem cells. Blood. 2005; 106:673-680.
44. Gilliland D G, Griffin J D. The roles of FLT3 in hematopoiesis and leukemia. Blood. 2002; 100:1532-1542.
45. Carow C E, Levenstein M, Kaufmann S H, et al. Expression of the hematopoietic growth factor receptor FLT3 (STK-1/Flk2) in human leukemias. Blood. 1996; 87:1089-1096.
46. Jordan C T. Unique molecular and cellular features of acute myelogenous leukemia stem cells. Leukemia. 2002; 16:559-562.
47. Jordan C T, Guzman M L. Mechanisms controlling pathogenesis and survival of leukemic stem cells. Oncogene. 2004; 23:7178-7187.
48. Xu Q, Thompson J E, Carroll M. mTOR regulates cell survival after etoposide treatment in primary AML cells. Blood. 2005; 106:4261-4268.
49. Jiffar T, Kurinna S, Suck G, et al. PKC alpha mediates chemoresistance in acute lymphoblastic leukemia through effects on Bcl2 phosphorylation. Leukemia. 2004; 18:505-512.
50. Kurinna S, Konopleva M, Palla S L, et al. Bcl2 phosphorylation and active PKC alpha are associated with poor survival in AML. Leukemia. 2006; 20:1316-1319.
51. Pandey P, Nakazawa A, Ito Y, Datta R, Kharbanda S, Kufe D. Requirement for caspase activation in monocytic differentiation of myeloid leukemia cells. Oncogene. 2000; 19:3941-3947.
52. Hass R, Pfannkuche H J, Kharbanda S, et al. Protein kinase C activation and protooncogene expression in differentiation/retrodifferentiation of human U-937 leukemia cells. Cell Growth Differ. 1991; 2:541-548.

53. Murray N R, Fields A P. Atypical protein kinase C iota protects human leukemia cells against drug-induced apoptosis. J Biol. Chem. 1997; 272:27521-27524.
54. Levis M, Small D. FLT3 tyrosine kinase inhibitors. Int J Hematol. 2005; 82:100-107.

Results

Figure 9:
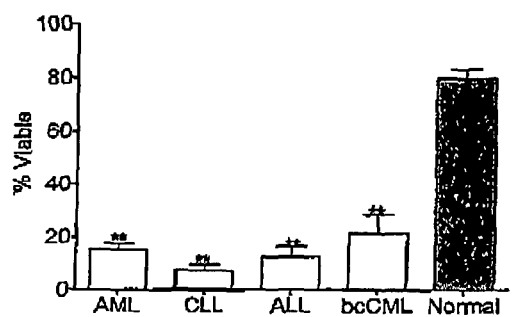
FIG. 9 TDZD-8 specifically induces cell death of primary leukemia specimens. Primary AML (n=37), CLL (n=12), ALL (n=6), bcCML (n=6) and normal specimens (n=13) obtained from BM (n=3), CB (n=7) or MPB (n=3) specimens were cultured for 18-24 hours in the presence of 20 μM TDZD-8. Cell viability was assessed by Annexin V/7-AAD staining. Percent viability is represented relative to untreated control. Leukemia specimens were significantly (p<0.001) more sensitive to TDZD-8 than normal specimens. Error bars represent the SEM. All assays were performed in triplicate.

TDZD-8 induces leukemia specific cell death. Initial studies were performed to determine the effects of TDZD-8 on different types of primary human leukemia (AML, blast crisis CML, CLL and ALL), as well as normal hematopoietic cells. FIG. 9 shows the percent viability relative to untreated controls for primary human specimens treated with 20 μM TDZD-8 for 24 hours. All forms of leukemia were strongly impaired by TDZD-8, with mean viability of 15% for AML (n=37), 7.2% for CLL (n=12), 12.4% for ALL (n=6) and 21.6% for bcCML (n=6). In contrast the cell viability for normal specimens was 79.5% (n=13). Moreover, the lack of toxicity towards normal specimens was not significantly different for CB, BM and MPB when each tissue type was analyzed separately (FIG. 14). Thus, the cytotoxicity of TDZD-8 was significantly ($p<0.001$) more specific to leukemia specimens. Given the broad efficacy towards leukemia cells, we further determined the range of activity for different types of tumor cells by submitting TDZD-8 for screening against the NCI-60 panel.[36] Interestingly, TDZD-8 activity was specific to cell lines derived from hematologic malignancies, where the average concentration to achieve 50% growth inhibition (GI50) was 8.3 μM (Table 1). All other tumor lines showed no growth inhibition up to concentrations of 100 μM. Together, these data indicate that while TDZD-8 is highly cytotoxic to leukemia and related diseases, the compound does not substantially harm normal hematopoietic cells or tumors derived from other non-hematopoietic tissues.

Figure 10:
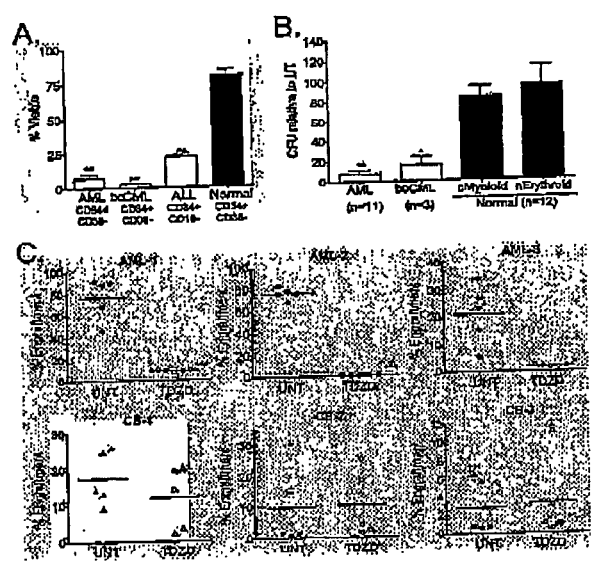
FIG. 10 TDZD-8 ablates leukemia progenitor and stem cells. (A) Primary AML (n=10), ALL (n=3), bcCML (n=3), and normal specimens (n=7) obtained from BM, CB or MPB specimens were cultured for 18-24 hours in the presence or absence of 20 μM TDZD-8. Cell viability was assessed by flow cytometry in CD34+CD38− populations for AML and bcCML (CML) and CD34+CD10− cells for ALL using Annexin V/7-AAD stain. Percent viability is represented relative to untreated control. Specificity to leukemia specimens was significant (p<0.01). Error bars represent the SEM. (B) primary cells from AML (n=11), bcCML (CML; n=3) and normal specimens (n=12) were treated for 18 hours in suspension culture, followed by plating in methylcellulose. Error bars represent the SEM. Percent of colony-forming units (CFU) are normalized to untreated controls. All assays were performed in triplicate. Specificity to leukemia specimens was significant (p<0.01, *p<0.05). (C) Percent engraftment for NOD/SCID mice that received a transplant with AML (upper panels) or normal CB (lower panels) cells after 18 hours of culture with or without 20 μM TDZD-8. Each circle or triangle represents a single animal analyzed at 6 weeks after transplantation. Each plot represents an independent AML or CB specimen. Mean engraftment is indicated by the horizontal bars. p<0.01, *p<0.001.

TDZD-8 anti-leukemia effects are observed at the progenitor and stem cell levels. While many agents show efficacy towards bulk tumor populations, eradication of more primitive stem and progenitor cells can represent a significant challenge. Given the established role of LSCs in several forms of leukemia,[1,3,4,37] we examined the effect of TDZD-8 on phenotypically described stem cells from AML, bcCML and ALL specimens. Treatment with 20 μM TDZD-8 for 24 hours resulted in a mean viability of 7.6% for CD34+CD38− from AML specimens (n=10); 2.8% for CD34+CD38− from bcCML specimens (n=3); and 22.3% for CD34+CD10− from ALL specimens (n=3) (FIG. 10A). In contrast, the viability of CD34+CD38− cells from healthy specimens (n=7) was 80.2% after TDZD-8 treatment (FIG. 10A, grey bar). Thus, the specificity of the compound for phenotypically described LSCs was highly significant ($p<0.001$). To determine whether TDZD-8 could also target functionally defined myeloid progenitor cells, we performed methylcellulose colony assays. FIG. 10B shows that the ability of normal specimens to form colonies was not substantially affected by treatment with 20 μM TDZD-8 (84.14% myeloid colonies and 94.79% erythroid colonies; n=12). In contrast, a significant decrease in colony formation was observed for both AML and blast crisis CML, with only 7.3% CFU for AML (n=11, $p<0.001$) and 16.1% CFU for bcCML (n=3, $p<0.01$) after TDZD-8 treatment. It should be noted that for 6 out of the 11 AML samples assayed, no colonies whatsoever were evident after treatment with TDZD-8. Further, we analyzed stem cell activity for AML and normal specimens using the NOD/SCID xenotransplant model.[38] These studies demonstrated that AML cells treated with 20 μM TDZD-8 for 18 hours significantly decreased their ability to engraft into NOD/SCID mice (FIG. 10C). Analysis of 3 independent specimens demonstrated engraftment of leukemic cells decreased to 11% ($p<0.001$), 1% ($p=0.001$) and 8.5% ($p<0.01$) respectively relative to untreated controls. In contrast, little to no effect on the engraftment of normal specimens (n=3) was observed after treatment with TDZD-8. Together these data demonstrate that TDZD-8 is highly cytotoxic towards leukemic but not normal hematopoietic progenitor and stem cells.

TDZD-8 activity involves oxidative stress. Previous studies have indicated that leukemia-specific agents may function via mechanisms involving the induction of oxidative stress.[39,14] Therefore, we performed studies to examine whether TDZD-8 might also modulate the oxidative state of target cells. Shown in FIG. 11A is labeling with the dye mBBr, which detects free thiol groups. Reduced labeling intensity signifies loss of free thiols, an indication of increased oxidative stress. Upon treatment with TDZD-8, reduction in mBBr labeling is evident in primary AML, ALL and CLL specimens as early as 30 minutes after exposure, suggesting rapid thiol depletion in the cell. Moreover, only slight changes in mBBr staining were observed in normal specimens. To further examine the role of oxidative state, we pretreated target cells with the anti-oxidant N-acetyl-cysteine (NAC), which completely blocked the cell death response in primary AML cells induced by TDZD-8 (FIG. 11B). Taken together, these data indicate that TDZD-8 induces oxidative stress and that this activity is important for the anti-leukemia properties shown above.

TDZD-8 anti-leukemia activity is observed with very rapid kinetics. We noted that changes in oxidative state (FIG. 11A) occurred with relatively rapid kinetics, suggesting that other cellular changes may also occur quickly. To further test the rate at which TDZD-8 may affect leukemic cells we performed additional studies using primary AML specimens to determine viability at various times post-exposure (0.5, 1, 2, 4, 6 and 24 hours). For comparison, parallel studies were performed with parthenolide (PTL), a drug we have previously shown can also specifically target primary human LSC.[14] As shown in FIG. 12A (left panel), primitive AML CD34+/CD38− cells treated with TDZD-8 displayed an extremely rapid loss of viability, with a mean time of only 2 hours to achieve ≥50% cell death. In contrast, PTL did not significantly change cell viability until 6 hours of treatment where the mean viability was still over 70% (FIG. 12A, right panel). The rapid cell death induced by TDZD-8 treatment was also observed for bulk leukemia blast populations, where an analysis of 17 primary specimens also showed a mean time of 2 hours to achieve ≥50% cell death (FIG. 12B). Interestingly, while all 17 specimens responded relatively fast, three specimens showed a particularly dramatic reduction in viability to below 30% within 30 minutes. We also tested lymphoid specimens and observed rapid cell death kinetics for primary CLL and ALL samples (both total blast populations and phenotypically described stem cells) (FIG. 15). Next we examined the minimum time of exposure required for the commitment of AML populations to cell death. For these studies, cells were treated with 20 μM TDZD-8 for varying times and then immediately washed and re-plated in fresh culture medium. Cell viability was evaluated 24 hours after initial treatment. Strikingly, as little as 30 minutes exposure to TDZD-8 was sufficient to commit primary human AML cells to death (FIG. 12C). The 30-minute exposure time was also sufficient to inhibit the ability of AML progenitor cells to form colonies in methylcellulose culture (FIG. 12D). Together, the data indicate that primary AML bulk and progenitor cell populations are irreversibly committed to cell death within 30 minutes of exposure to TDZD-8.

The short exposure time for commitment to cell death suggests that TDZD-8 may be rapidly binding and/or internalized by cells. Since the hydrophobic chemical structure of TDZD-8 predicts that the drug is likely to intercalate in membranes, experiments were performed to analyze plasma membrane integrity. For this purpose, several nucleic acid dyes of varying sizes were employed (YoPro-1, Hoescht-33342, 7-AAD and propidium iodide (PI)). The uptake of smaller dyes, YoPro-1 and Hoescht-33342, can be altered by relatively moderate changes in membrane permeability, whereas larger dyes such as 7-AAD and PI are only internalized when profound loss of membrane integrity occurs. FIG. 12E shows a representative example of a primary AML specimen treated with TDZD-8 for 15 minutes and analyzed by nucleic acid dye labeling and multispectral imaging flow cytometry (Amnis Imagestream). The left panels show dye uptake analysis in control or TDZD-8 treated cells where R1 represents intact cells (impermeable to YoPro-1), R2 shows cells with compromised membrane integrity (YoPro-1 permeable), and R3 represents dead cells (permeable to YoPro-1 and 7-AAD). The percent of YoPro-1 positive cells (R2) increased from 7% to 78% upon treatment with TDZD for 15 min. In addition, cells were also labeled with anti-CD45 to delineate the plasma membrane and the cell permeable DNA dye Draq5 to identify the nucleus. FIG. 12E (right panel) shows representative pictures of cells present in the R1, R2 and R3 gates, where the nuclear localization of YoPro-1 is evident in R2 but not R1. Additional studies in FIG. 12F demonstrate that the rapid uptake of YoPro-1 observed for primary AML cells is not evident in normal specimens (BM or CB). These data indicate that TDZD-8 mediates a rapid alteration in membrane permeability in primary AML cells but not in normal hematopoietic cells.

With respect to the death mechanism, TDZD-8 treated cells show a rapid increase in Annexin V labeling, a marker of apoptosis (data not shown). Since loss of membrane integrity and Annexin V binding are early events associated with apoptosis, we tested downstream events involved in caspase-dependent apoptotic events (e.g. pro-caspase and PARP cleavage). Interestingly, no cleavage of pro-caspases 3, 8 or PARP was detected (data not shown). Moreover, no abrogation of death was observed upon treatment with the pan-caspase inhibitor Z-VAD (FIG. 12G, white bars). These data suggest that death occurs via a caspase-independent pathway.

TDZD-8 activity as a kinase inhibitor. TDZD-8 has been reported to be a GSK-3β kinase inhibitor ($IC_{50}$=2 μM) and to not significantly affect the activities of Cdk-1/cyclin B, CK-II, PICA, and PKC ($IC_{50}$>100 μM).[24] Therefore, to determine whether the anti-leukemia activity observed with TDZD-8 involves GSK3β inhibition, we tested other commercially available GSK3β inhibitors. Seven of the eight agents tested failed to induce AML cell death (Table 2). The single other GSK3β inhibitor (2-chloro-1-(4,5-dibromo-thiophen-2-yl-ethanone) that could induce AML cell death was also toxic to normal cells. In addition, we tested different compounds that share the thiazolidinedione ring structure and did not observe the AML-specificity or cell death kinetics obtained with TDZD-8 (Table 2). Since the concentrations that induce leukemia specific cell death are 10 times higher than the IC50 reported for inhibition of GSK3β, it is likely that the TDZD-8 anti-leukemia activity is due to an off-target effect. To test this hypothesis, a commercial kinase profiling service was employed to identify other potential targets of TDZD-8. A broad range of 44 different transmembrane and intracellular kinases was examined at a drug concentration of 20 μM. Greater than 90% inhibition was observed for 14 different classes of kinase. Of those, the most evident enzymes with potential ties to hematologic malignancy were PKC and FLT3. Notably, other related kinases implicated in hematologic diseases (c-kit, PDGF-R, Jak2, Src, and Tie2) showed little to no inhibition. To further examine PKC and FLT3, preliminary studies were performed to examine the activity of each in primary specimens and in response to drug treatment.

Figure 13:
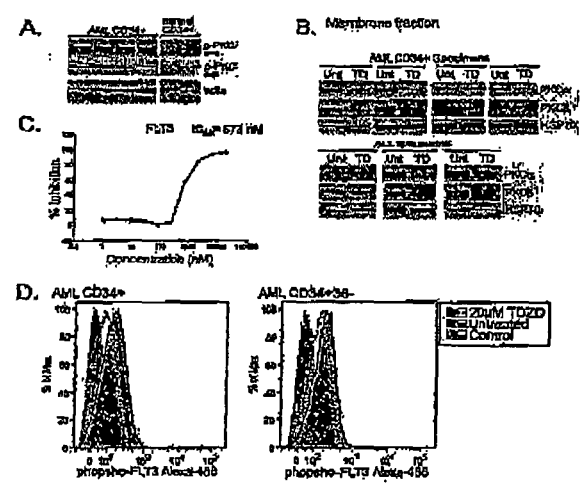
FIG. 13 TDZD-8 inhibits PKC and FLT3 in primary AML specimens. (A) Immunoblots for CD34+ AML and normal BM specimens to determine PKC phosphorylation. Actin is shown as loading control. (B) Primary CD34+ AML and ALL specimens treated with TDZD-8 for 1-hour were processed to obtain membrane fractions. Immunoblots were performed to determine PKCα and PKCβ levels in the membrane. HSP70 is shown as a control. (C) Titration curve and IC50 value for FLT3 kinase assay. (D) Overlays of flow cytometric analysis for phospho-FLT3 in primary AML specimens. Light gray-solid line histograms represent untreated cells. Dotted line histograms represent TDZD-8 treated cells. Dark gray-no line histogram represent controls. Cells were processed for analysis 30 minutes after the addition of drug. CD34+ (31% inhibition; left panel) and CD34+CD38− (29.5% inhibition; right panel) populations.

First, since PKC was previously reported to not be a target of TDZD-8 (IC50>100 μM), we analyzed one family member from each of the three major PKC classes (conventional, novel, and atypical). The in vitro IC50 for PKC isoforms was: PKC beta I=1.4 μM, PKC delta=1.1 μM, and PKC iota=5.5 μM. Thus, at least in vitro, TDZD-8 appears to be a broad inhibitor of the PKC family. As a control for drug activity, GSK3β was also tested, and consistent with previous reports had an IC50 of 1.4 μM. Next, to examine the activity of PKC in primary cells, immunoblots of purified CD34+ populations from AML and normal BM specimens were performed. As shown in FIG. 13A, the levels of both total and phosphorylated-PKC were much higher in primary CD34+ AML specimens compared to normal controls, suggesting a role for the PKC family in primitive leukemic cells. Since active PKCs are localized in the plasma membrane[40,41] and PKCα and PKCβ plasma membrane localization has been reported in leukemia cell lines,[42] we examined their levels upon TDZD-8 treatment. FIG. 13B shows that plasma membrane localized PKCα and β decreases with TDZD-8 exposure, suggesting that TDZD-8 induces PKC inactivation in primary CD34+ AML and ALL cells. We did not observe a difference in the levels of HSP70 suggesting that reduction of PKC in the membrane is not due to a general loss of membrane proteins. The data in FIGS. 13A and B indicates the PKC family members are active in primary AML cells and that TDZD-8 potentially inhibits their function.

To examine the inhibitory effect of TDZD-8 on FLT3 activity, titration assays for FLT3 kinase activity were performed to estimate the in vitro IC50 of TDZD-8. FIG. 13C shows the titration curve, which demonstrates an IC50 of 673 nM in vitro. Next, to assess whether TDZD-8 inhibitory FLT3 activity could be detected in vivo, FACS analyses were performed to measure the phospho-specific (i.e. activated) FLT3 form. As shown in FIG. 13D, phosphorylated FLT3 is readily detected in primary AML specimens (as previously reported[43-45]), and treatment with TDZD-8 induced a ~30% reduction in phosphorylation for both CD34+ and CD34+, CD38− populations. These data suggest TDZD-8 may also function as an intracellular inhibitor of FLT3 activation.

In the present study we describe unique anti-leukemia properties of the compound TDZD-8, which was originally developed as a non-ATP competitive inhibitor of GSK3β. The compound has undergone preclinical analysis as a cyto-protective agent in numerous models, including studies of type-2 diabetes, Alzheimer's disease, spinal cord injury, and several forms of inflammation. Our findings add an entirely new dimension to the activities of TDZD-8 by demonstrating that the compound selectively induces death of several major forms of leukemia cells, including malignant myeloid stem and progenitor populations, while sparing normal hematopoietic tissue. Further, the rate of cell death is exceptionally fast, with most toxicity evident within 1-6 hours. Based on these data, we believe that TDZD-8 may function via a novel mechanism to induce death of malignant hematopoietic cells.

Another striking feature of TDZD-8 is its apparent affinity to target cells. Experiments demonstrated that exposure to the drug of only 30 minutes was sufficient to mediate all cytotoxic activity. Additional preliminary data indicates that treatments as brief as 5 minutes may also be effective (data not shown). Given the hydrophobic nature of TDZD-8, it appears that the molecule is rapidly inserted into cellular membranes. This premise in turn indicates that one component of the drug's mechanism might be a direct effect on the plasma membrane. Subsequent studies confirmed that TDZD-8 induces a rapid change in membrane integrity, such that small nucleic acid dyes are readily internalized. These findings support the concept the TDZD-8 directly modulates membrane integrity.

Aside from the novel membrane-directed biology described above, TDZD-8 also functions as a multi-kinase inhibitor. Among those targets is, as described, GSK3β.[24] Notably, analysis of several other known GSK3β inhibitors failed to induce leukemia-specific cell death (Table 2), suggesting that the activity of TDZD-8 is independent of GSK3β or at least combined with other activities. Other targets of TDZD-8, both in vitro and in vivo, are PKC family members and FLT3. PKC is known to play a role in growth and differentiation of hematopoietic cells.[42] Moreover, it has been reported that PKCα over-expression confers chemoresistance to leukemia cells and is associated with poor survival,[49-50] and that PKCβ is important for differentiation of HL-60 and U937 cells.[51,52] In addition, PKC$_t$ is involved in protection of K562 cells against drug-induced apoptosis.[53] These findings support a role for PKC in malignant hematopoiesis and suggest the PKC family may represent an important target for therapy. Similarly, aberrant activation of FLT3 is a well described feature of AML cell types and inhibition of FLT3 clearly mediates an anti-leukemic effect in several systems.[44,54] Thus, the activity of TDZD-8 towards FLT3 and PKC are potentially important component of its overall mechanism of action.

Figure 12:
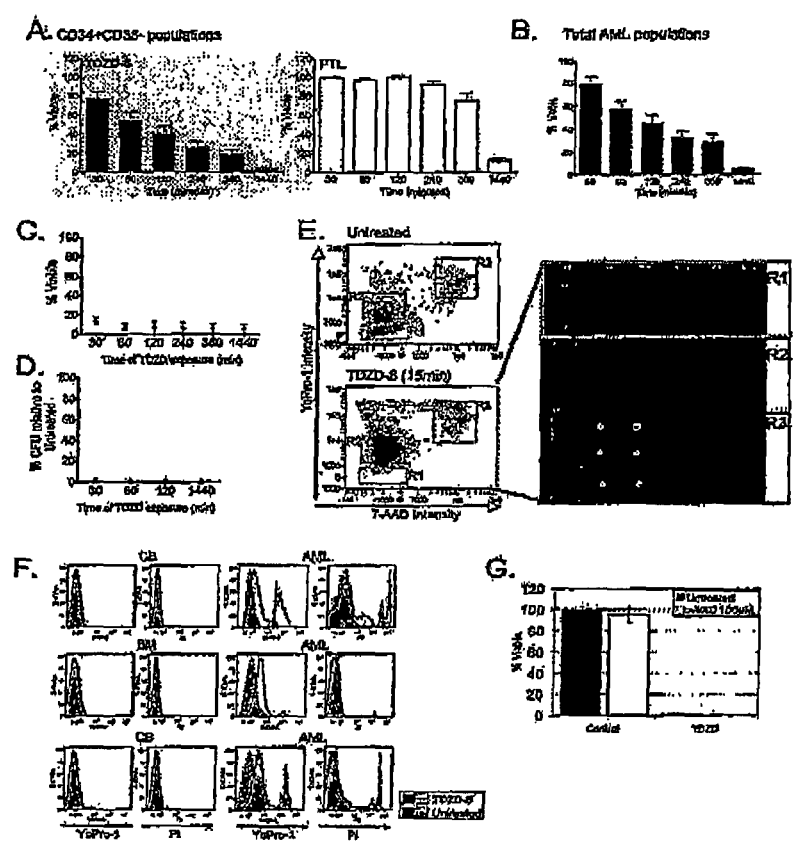
FIG. 12 TDZD-8 induces cell death with extremely rapid cell death kinetics demonstrating loss of membrane integrity. (A) Percent viability assessed at the indicated time points for CD34+CD38− populations of primary AML specimens (n=8) treated with TDZD-8 (left panel, black bars) or PTL (right panel, white bars). Percent viability is represented relative to untreated control. (B) Percent viability assessed at the indicated time points for unfractionated primary AML specimens (n=17) treated with TDZD-8. Percent viability is shown relative to untreated controls. Error bars represent SEM. (C) Cells were treated with 20 μM TDZD-8 for the indicated periods of time, then washed and placed in culture until analysis at 24 hours. Percent viability represented relative to untreated control. (D) Percent CFU relative to untreated control. Cells were washed and placed in methylcellulose culture medium at the indicated time points after the addition TDZD-8. (E) Loss of membrane integrity assessed by YoPro-1 uptake after 15 min of TDZD-8 treatment. Multispectral imaging flow cytometry demonstrates the internalization of YoPro-1. Cells were stained with CD45 to delineate the plasma membrane and with the cell permeable DNA dye Draq5 to identify the nucleus. (F) Flow cytometric histograms for YoPro-1 and PI overlaying TDZD-8 treated (20 μM for 15 min) normal mononuclear cells or primary AML cells over untreated controls. (G) Percent viability of primary AML cells pre-treated with Z-VAD (white bars) for 1 h prior the treatment with TDZD-8 20 μM. Viability was determined 24 hours after the addition of TDZD-8. Error bars represent the SEM.

Finally, we note that previous studies have described TDZD-8 as a moderate NF-κB inhibitor,[27-29,32] an activity we have confirmed in leukemia cells (data not shown). Further, our data indicate the compound is a strong oxidant (FIG. 11). Therefore, TDZD-8 fulfills the two criteria described above that have previously been reported for regimens that selectively target LSC (i.e. inhibition of NF-κB and induction of oxidative stress).[47] However, as shown in FIG. 12, in addition to the established mechanisms of LSC death induction TDZD-8 also confers a rapid alteration in membrane permeability for malignant cells of hematologic origin. Thus, it is indicated that loss of membrane integrity substantially accelerates the rate of cell death and is integral to the overall effects observed for TDZD-8.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

TABLE 1

| Cell lines | $Log_{10}$ GI50 | μM |
|---|---|---|
| NCI-60 screen | | |
| Leukemia | | |
| CCRF-CEM | −4.94 | 11.5 |
| HL-60 | −6.63 | 0.2 |
| K-562 | −5.19 | 6.5 |
| RPMI-8226 | −4.63 | 23.4 |
| SR | −8 | 0.01 |
| Non-small cell lung cancer | | |
| 9 cell lines | −4 | >100.0 |
| Colon cancer | | |
| 7 cell lines | −4 | >100.0 |
| CNS cancer | | |
| 6 cell lines | −4 | >100.0 |
| Melanoma | | |
| 8 cell lines | −4 | >100.0 |
| Ovarian cancer | | |
| 5 cell lines | −4 | >100.0 |
| Renal cancer | | |
| 7 cell lines | −4 | >100.0 |
| Prostate cancer | | |
| 2 cell lines | −4 | >100.0 |
| Breast cancer | | |
| 7 cell lines | −4 | >100.0 |

TABLE 2

Inhibitor tested on primary AML and Normal specimens

| Activity | Compound | Cytotoxic AML | Cytotoxic Normal | Rapid kinetics |
|---|---|---|---|---|
| GSK-3β inhibitor | TDZD-8 (4-Benzyl-2-methyl-1,2,4-thiadiazolidine-3,5-dione_ | Yes | No | Yes |
| GSK-3β inhibitor | BIO | No | No | No |
| GSK-3β inhibitor | (5-Methyl-1H-pyrazol-3-yl)-(2-phenylquinazolin-4-yl)amine | No | No | No |
| GSK-3β inhibitor | 2-Chloro-1-(4,5-dibromo-thiophen-2-yl)-ethanone | Yes | Yes | No |
| GSK-3β inhibitor | TWS119 | No | No | No |
| GSK-3β inhibitor | SB-216763 | No | No | No |
| GSK-3β inhibitor | AR-A014418 | No | No | No |
| GSK-3β inhibitor | 1-Azakenpaullone | No | No | No |

TABLE 2-continued

Inhibitor tested on primary AML and Normal specimens

| Activity | Compound | Cytotoxic AML | Cytotoxic Normal | Rapid kinetics |
|---|---|---|---|---|
| GSK-3β inhibitor thiazolidin ring | 2,4-Dibenzyl-5-oxothiadiazolidine-3-thione | No | No | No |
| (thiazolidinedione ring) | Anthrax Lethal Factor protease inhibitor | No | No | No |
| (thiazolidinedione ring) | 2,4-thiazolidinedione | No | No | No |
| (thiazolidinedione ring) PPARα/γ agonist | DRF 2519 | No | No | No |
| (thiazolidinedione ring) PPARα/γ agonist | Troglitazone | Yes | Yes | No |
| (thiazolidinedione ring) Erk inhibitor | -(2-Aminoethyl)-5-((4-ethoxyphenyl)methylene)-2,4-thiazolidinedione, HCl | No | No | No |
| (thiazolidinedione ring) PI3-K inhibitor | 5-(2,2-Difluoro-benzo[1,3]dioxol-5-ylmethylene)-thiazolidine-2,4-dione | No | No | No |

TABLE 3

TDZD-8 as test compound

| Kinase Tested | % Inhibition mean |
|---|---|
| ABL1 | 70 |
| AKT1 (PKB alpha) | 102 |
| BTK | 72 |
| CDK1/cyclin B | 15 |
| CHEK1 (CHK1) | 87 |
| CSNK1G2 (CK1 gamma 2) | 22 |
| CSNK2A1 (CK2 alpha 1) | 27 |
| DYRK3 | 85 |
| EGFR (ErbB1) | 1 |
| EPHA2 | 3 |
| ERBB2 (HER2) | 12 |
| FGFR1 | 1 |
| FLT3 | 99 |
| GSK3B (GSK3 beta) | 98 |
| GSK3B (GSK3 beta) | 99 |
| IGF1R | -2 |
| INSR | 9 |
| IRAK4 | 8 |
| JAK3 | -1 |
| KDR (VEGFR2) | 100 |
| KIT | -6 |
| LCK | -9 |
| MAP2K1 (MEK1) | 80 |
| MAP4K4 (HGK) | 99 |
| MAPK14 (p38 alpha) | 97 |
| MAPK3 (ERK1) | 61 |
| MAPKAPK2 | 99 |
| MET (cMet) | 90 |
| NTRK1 (TRKA) | -9 |
| PDGFRB (PDGFR beta) | -4 |
| PHKG2 | 80 |
| PIM1 | 95 |
| PRKACA (PKA) | 18 |
| PRKCA (PKC alpha) | 102 |
| PRKCB1 (PKC beta I) | 98 |
| PRKCB1 (PKC beta I) | 98 |
| PRKCB2 (PKC beta II) | 99 |
| PRKCD (PKC delta) | 102 |
| PRKCE (PKC epsilon) | 99 |
| PRKCG (PKC gamma) | 103 |
| PRKCH (PKC eta) | 104 |
| PRKCI (PKC iota) | 100 |
| PRKCN (PKD3) | 94 |
| PRKCQ (PKC theta) | 101 |
| PRKCZ (PKC zeta) | 100 |
| PRKD1 (PKC mu) | 97 |
| RET | 34 |
| ROCK1 | 113 |
| RPS6KA3 (RSK2) | 101 |
| SRC | 27 |
| STK6 (Aurora A) | 99 |
| SYK | 99 |
| TEK (Tie2) | 9 |

What is claimed is:

1. A method of treating a disorder in a subject, wherein the disorder is lymphoma, multiple myeloma, leukemia cell growth; hematologic malignancies, acute myelogenus leukemia (AML), blast crisis leukemia, acute lymphocytic leukemia (ALL), or chronic lymphocytic leukemia (CLL), comprising administration of 4-benzyl-2-methyl-1,2,4-thiadiazolidine-3,5-dione (TDZD-8) to the subject.

2. A method for treating leukemia in a subject comprising administering to the subject a compound of Formula (II):

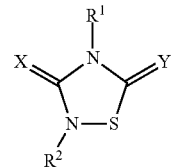

or a salt thereof; or a pro drug, or a salt of a prodrug thereof; or a hydrate, solvate, or polymorph thereof; wherein:
$R^1$ or $R^2$ is independently selected from methyl, ethyl, n-propyl, i-propyl, n-butyl, t-butyl, n-pentyl, benzyl, halomethyl, and haloethyl, and the other $R^1$ or $R^2$ is independently selected from benzyl, ethyl, and phenethyl, wherein the benzyl group may be optionally substituted by one substituent selected from the group consisting of methyl, methoxy, phenyl, or aminomethyl; and X and Y are each =O.

3. The method of claim 2, wherein the compound has the formula represented by the structure:

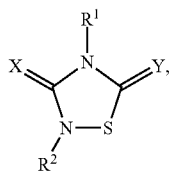

wherein $R^2$ is selected from Me, Et, n-propyl, n-Bu, Bn, $CH_2CH_2Ph-$, EtCl, and EtBr; and wherein $R^1$ is selected from Me, Et, i-Pr, n-Pr, Bn, 4-methoxybenzyl, 4-methylbenzyl, 4-aminomethylbenzyl, and 3-aminomethylbenzyl; provided that one $R^1$ and $R^2$ is independently alkyl and the other of $R^1$ and $R^2$ is independently alkyl substituted with aryl.

4. The method of claim 2, wherein the compound has formula represented by the structure:

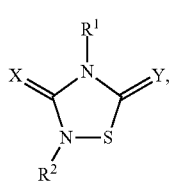

wherein $R^2$ is selected from Bn and $CH_2CH_2Ph$; and
wherein $R^1$ is selected from Me, Et, i-Pr, and n-Pr.

5. The method of claim 2, wherein the compound is 4-benzyl-2-methyl-1,2,4-thiadiazolidine-3,5-dione (TDZD-8).

* * * * *